United States Patent [19]
Riedl et al.

[11] Patent Number: 5,601,867
[45] Date of Patent: Feb. 11, 1997

[54] METHOD AND APPARATUS FOR GENERATING FINGERPRINTS AND OTHER SKIN PRINTS

[75] Inventors: Harold R. Riedl, Adelphi; Robert E. Jehle, Silver Spring, both of Md.

[73] Assignee: The United States of America as represented by the Secretary of the Navy, Washington, D.C.

[21] Appl. No.: 493,608

[22] Filed: Jun. 22, 1995

[51] Int. Cl.⁶ .................... A61B 5/117; B41K 1/00
[52] U.S. Cl. .................... 427/1; 427/336; 427/384; 118/31.5
[58] Field of Search .................... 427/1, 336, 384; 118/31.5

[56] References Cited

U.S. PATENT DOCUMENTS

| | | | |
|---|---|---|---|
| 2,082,735 | 6/1937 | Heinecke | 41/41 |
| 3,533,823 | 10/1970 | Newkirk et al. | |
| 3,539,375 | 11/1970 | Baum. | |
| 3,674,535 | 7/1972 | Blose et al. | |
| 3,746,675 | 7/1973 | Blose et al. | 260/23 |
| 3,953,659 | 4/1976 | Truitt | 428/511 |
| 4,151,748 | 5/1979 | Baum | 73/356 |
| 4,181,771 | 1/1980 | Hanson et al. | 428/327 |
| 4,246,318 | 1/1981 | Baum | 428/411 |
| 4,260,646 | 4/1981 | Farrell et al. | 427/1 |
| 4,379,178 | 4/1983 | Meadows et al. | 427/1 |
| 4,436,920 | 3/1984 | Sato et al. | 549/227 |
| 4,470,057 | 9/1984 | Glanz | 346/209 |
| 4,480,052 | 10/1984 | Ichijima et al. | 346/208 |
| 4,535,347 | 8/1985 | Glanz | 346/208 |
| 4,794,102 | 12/1988 | Petersen et al. | 503/209 |
| 4,870,047 | 9/1989 | Glanz et al. | 503/209 |
| 4,879,134 | 11/1989 | Vassiliades | 427/1 |
| 4,983,415 | 1/1991 | Arnat et al. | 427/1 |
| 5,009,919 | 4/1991 | Vassiliades | 427/1 |
| 5,071,821 | 12/1991 | Smith et al. | 503/208 |
| 5,173,477 | 12/1992 | Commandeur et al. | 503/208 |
| 5,249,370 | 10/1993 | Stanger et al. | 34/22 |
| 5,260,252 | 11/1993 | Frangie et al. | 503/206 |
| 5,288,688 | 2/1994 | Kawakami et al. | 503/217 |
| 5,290,702 | 3/1994 | Chang | 436/2 |
| 5,290,704 | 3/1994 | Chang | 436/128 |
| 5,318,938 | 6/1994 | Hampl, Jr. et al. | 503/200 |
| 5,330,231 | 7/1994 | Godfrey | 427/1 |
| 5,354,724 | 10/1994 | Hoffmann et al. | 503/209 |

Primary Examiner—Janyce Bell
Attorney, Agent, or Firm—Howard Kaiser

[57] ABSTRACT

Inkless skin printing apparatus and method featuring unique cooperation of a common, harmless, odorless solvent in association with ordinary thermal (fax) paper material. The skin area is coated with a substance which includes the solvent and then impressed onto and withdrawn from the thermal paper, thereby visibly forming a developing impression on the thermal paper which eventually fully develops into a quality skin print. Heat application to the developing impression may serve to accelerate and/or enhance the development. Skin prints such as fingerprints are generated according to this invention with "no muss, no fuss, no-clean-up-required" neatness and efficiency, and if desired with on-location portability.

29 Claims, 10 Drawing Sheets

METHOD AND APPARATUS FOR GENERATING FINGERPRINTS AND OTHER SKIN PRINTS

The invention described herein may be manufactured and used by or for the Government of the United States of America for governmental purposes without the payment of any royalties thereon or therefor.

BACKGROUND OF THE INVENTION

The present invention relates to method and apparatus for imaging skin, more particularly to method and apparatus for imaging ridge patterns on fingers and other areas of human skin without using conventional pigment-type ink.

For some time the human fingerprint has been recognized as a scientifically sound basis for identification which is unique to the individual. Fingerprinting is a proven valuable tool in law enforcement, government security and many other contexts wherein conclusive determination or establishment of a person's identity is of import.

The conventional methodology for ink fingerprinting involves first coating the ridged skin area of a finger with wet dark ink and then pressing the coated area upon a light surface, thereby leaving an impression which will eventually dry into a permanent image. Afterwards a cleansing agent for removing the ink from the affected skin areas is applied.

Most people who have been subjected to fingerprinting procedures which utilize ink will agree that such procedures are cumbersome and messy. Even when inadvertent ink soiling (e.g., of skin, clothing, documents, etc.) has been successfully avoided, such inking procedures offend many a person's sensibilities of neatness. Furthermore, once the fingerprint is formed the wet ink does not dry immediately and the fingerprint may therefore be vulnerable to smearing or smudging until it completely dries.

Messiness is a characteristic which has heretofore contributed to limiting the utilization of fingerprinting as an identification tool to more formal or specialized contexts. Reduction of messiness would open the door to more casual or prevalent utilization of fingerprinting.

For example, in many everyday situations a person's identity is verified by means of his or her signature in order that a business or organization may extend credit to that person. Signature verification, at best, is an inexact science which brings to bear the supposed perceptiveness of a handwriting "expert" who seeks to distinguish true signature matches from signature forgeries. Fingerprint verification, on the other hand, is not subject to such vagary and conjecture. A fingerprint cannot be forged. A fingerprinted signature (even a single fingerprint or thumbprint), unlike a handwritten signature, is foolproof and indisputable; it represents inalterable and inimitable physical characteristic, rather than alterable and imitable behavioral characteristic.

The need may also arise in some official capacities to perform fingerprinting "in the field." Governmental officials and agents, both military and civilian, such as police officers, investigators and casualty identification personnel, may experience the necessity or desirability of conveniently and facilely fingerprinting a person "on the spot" so as to avoid traveling to a designated fingerprinting station. Conventional ink fingerprinting systems, which implement, e.g., inkpads, cards and ink cleansers, do not readily lend themselves to on-site performance.

Various "inkless" fingerprinting methods which depart from conventional pigment-type ink fingerprinting have been disclosed, e.g., by Heinecke U.S. Pat. No. 2,082,735, Newkirt et al. U.S. Pat. No. 3,533,823, Meadows et al. U.S. Pat. No. 4,379,178 and Stanger et al. U.S. Pat. No. 5,249,370.

SUMMARY OF THE INVENTION

In view of the foregoing, it is an object of the present invention to provide skin printing method and apparatus which do not utilize conventional pigment-type ink.

It is a further object of the present invention to provide such method and apparatus which succeed in generating a quality skin print.

It is another object of this invention to provide such method and apparatus wherein the skin print is administered relatively neatly.

It is a further object of this invention to provide such method and apparatus wherein the skin print is administered quickly.

It is another object of the present invention to provide such method and apparatus wherein the skin print is administered easily.

Another object of this invention is to provide such method and apparatus which admit of portability.

A further object of this invention is to provide such method and apparatus which admit of on-location practice.

A further object of this invention is to provide such method and apparatus which are economical.

Another object of the present invention is to provide such method and apparatus wherein the maturing skin print demonstrates some resistance to smearing or smudging.

Another object of this invention is to provide such method and apparatus which are harmless and non-toxic.

The present invention provides method for generating a print of human skin. The method of this invention comprises coating an area of the skin with a substance which includes an organic solvent, impressing the coated skin area onto an image recorder, and withdrawing the coated skin area from the image recorder.

For many embodiments of this invention, coating the skin area includes contacting the skin area with an organic solvent which is contained by a matrix. The matrix according to this invention is, depending on the embodiment, either of two basic types, viz., a "mechanical" matrix or a "chemical" matrix. The matrix serves as a vehicle for delivering or permitting access to the organic solvent contained by the matrix.

The image recorder includes a substrate, an electron-donating chromogenic composition and an electron-accepting color developer composition which are dispersed on the substrate, and a binder material which is substantially soluble to the organic solvent in the image producer and which generally maintains separation of the electron-donating chromogenic composition and the electron-accepting developer composition until the pressing of the coated skin area onto the image recorder.

The electron-donating chromogenic composition and the electron-accepting developer composition are the co-reactive color-forming compositions. The binder material serves to prevent co-reaction of the co-reactive color-forming compositions until the binder material commences to be solubilized by the organic solvent. For many embodiments of the present invention, the image recorder includes conventional, commercially available thermal paper; for some embodiments, the image recorder is or essentially is commercially available thermal paper. The thermal paper provides the substrate, binder material, electron-donating chromogenic composition and electron-accepting developer composition.

Upon impressing the coated skin area onto the image recorder, some of the image recorder's binder material is solubilized by at least some of the organic solvent which is included in the quantity of substance with which the skin area has been coated; for some embodiments of this invention, the quantity of substance with which the skin area has been coated consists of or essentially consists of the organic solvent. The solubilized binder material ceases to maintain separation of some of the image recorder's chromogenic composition and some of the image recorder's developer composition, thereby forming a developing impression on the image recorder. The developing impression is visibly formed on the image recorder upon the withdrawing of the coated skin area from the image recorder. The developing impression eventually fully develops into the skin print.

In tests performed by the U.S. Navy, it was found that the application of heat may be helpful. It may thus be preferable for some embodiments that the method of this invention further comprises applying heat to the image recorder in the vicinity of the developing impression. Although not wishing to be bound by theory as to why heat application may result in manifest betterment of the print, it is believed that heat application may serve to accelerate and/or enhance the breakdown of the binder in the image recorder; improvement in dissolution of the binder by the solvent may result in improvement in interaction of the color-producing compositions. It is also theorized that, perhaps for some such embodiments, heat application may instead or additionally serve to directly chemically enhance the color-producing interaction of the electron-donating chromogenic composition and the electron-accepting composition.

The present invention also provides apparatus for generating a print of human skin, comprising an image producer and an image recorder. For many embodiments the image producer is housed in a first compartment or included in a first unit and the image recorder is housed in a second compartment or included in a second unit, and for some such embodiments these compartments or units are combined in a single apparatus. The image producer includes a matrix and an organic solvent which is contained by the matrix. An area of the skin may be coated by a quantity of substance which includes a portion of the organic solvent. The image recorder may be impressed upon and withdrawn from by the coated skin area. When the image recorder is thus impressed upon, some of the image recorder's binder material is solubilized by at least some of the organic solvent which is included in the quantity of the substance with which the area of the skin has been coated. Some embodiments further comprise means for applying heat to the image recorder, either in the vicinity of the developing impression which will be formed on the image recorder, or directed toward the developing impression which has been formed, generally more or less visibly so, on the image recorder once the coated skin area has been withdrawn therefrom.

Chang U.S. Pat. No. 5,290,702, entitled "Method of Detecting and Mapping Organic Solvent-Containing Materials on a Surface," and Chang U.S. Pat. No. 5,290,704, entitled "Method of Detecting Organic Solvent Vapors," are incorporated herein by reference. Chang '702 and '704 disclose utilization of material which is described as "chromogenic record" material or "thermally-responsive record" material, and which is well known in the art and typified as conventional, commercially available thermal paper. Chromogenic or thermally-responsive record material has basic chromogenic composition and acidic developer composition contained by a binder substance on a substrate whereby the melting or softening of the binder substance, conventionally caused by heating, permits the chromogenic composition and acidic developer composition to react and thereby produce colored marking.

Chang '702 and '704 disclose use of "chromogenic record material" or "thermally-responsive record material" for what Chang '702 and Chang '704 term, respectively, a "chromogenic solvent detector" and a "solvent vapor detector." According to Chang '702 and '704, the "solvent vapor detector" or "chromogenic solvent detector" includes a substrate covered with a binder means having dispersed therein two kinds of mutually interactive color-forming compositions, viz., an electron-donating chromogenic composition (also referred to as an "electron donating color former," an "electron donating dye precursor" or a "non-polymeric colorless dye") and an electron-accepting composition (also referred to as a "developer" or an "acidic developer"). The binder means is substantially soluble to the organic solvent or organic solvent vapor being detected and maintains separation of the two color-forming compositions until the binder means is solubilized by the organic solvent or organic solvent vapor.

As used herein in connection with the present invention, the term "organic solvent" refers to any substance capable of dissolving another substance. The organic solvent is or includes at least one fundamental solubilizing chemical constituent which can act to solubilize the other substance. The organic solvent thus may include one fundamental solubilizing chemical constituent or may include a combination of two or more distinct fundamental solubilizing chemical constituents. For example, a solution which includes propylene glycol and isopropanol may be described herein as a single organic solvent with respect to thermal paper binder material, albeit that both propylene glycol and isopropanol are each independently solubilizingly active with respect to the thermal paper binder material. The organic solvent may include at least one ingredient which is not solubilizingly active with respect to the thermal paper binder material. Hence, for example, an organic solvent may include ingredients "A," "B," "C," "D" and "E," albeit that only ingredient "A" is solubilizingly active with respect to the thermal paper binder material.

The term "image producer" as used herein in connection with the present invention refers to an entity which accessibly includes an organic solvent. In practicing most embodiments of the present invention, the image producer includes an organic solvent and a matrix. At least a portion of the image producer's organic solvent is included in the quantity of substance which is used for coating the skin area. Practice of most embodiments requires containment of the organic solvent by a "matrix," the matrix thus serving to deliver or make accessible the portion of the organic solvent which is included in the quantity of substance with which the skin area is to be coated.

The term "matrix" as used herein refers to an entity which effectuates containment of an organic solvent. The term "mechanical matrix" as used herein in connection with the present invention refers to a matrix which effectuates physical containment of an organic solvent, i.e., containment by material which is macroscopically distinct from the organic solvent. The term "chemical matrix" as used herein in connection with the present invention refers to a matrix which is a macroscopically homogenous solvent-matrix material.

The term "image recorder" as used herein in connection with the present invention refers to an entity which includes a substrate, a binder material, an electron-donating chromogenic composition and an electron-accepting developer composition. In other words, an "image recorder" as used herein refers to an entity which includes "chromogenic record material" or "thermally-responsive record material"; such record materials are disclosed by Chang '702 and '704 and are well known in the art. The "chromogenic record material" or "thermally-responsive record material" provides the substrate, binder material, electron-donating chromogenic composition and electron-accepting composition.

The term "thermal paper" or "thermal paper material" as used herein refers to chromogenic or thermally-responsive record material which is in sheet form, such as, but not limited to, thermal papers or thermal paper materials which are conventionally used and commercially available. The "thermal paper" or "thermal paper material" provides the substrate, binder material, electron-donating chromogenic composition and electron-accepting composition. For many embodiments of the present invention, the image recorder is or includes a sheet of conventional, commercially available "thermal paper"(also commonly referred to as "thermal fax paper" or just "fax paper"), which still enjoys fairly prevalent use for electronic photocopy machines and especially for electronic facsimile ("fax") machines, despite the advent of "plain paper" technologies for such machines.

The "binder means" disclosed by Chang '702 and '704 is any or all of the material taken collectively which may include different constituents and which may perform any of several functions. The binder means may, for example, serve to improve the adhesion of the two color-forming compositions to the substrate, protect the color-forming compositions from external forces, and/or encompass the microencapsulation of the color-forming compositions. The term "binder material" as used herein refers collectively to the material which encompasses all that is encompassed by the "binder means" disclosed by Chang '702 and '704, and refers especially to such portion or portions of the binder material as are necessary for solubilization in accordance with the present invention. The most important function of the binder material as pertains to the present invention is to keep the color-forming compositions apart until the binder material is solubilized by the organic solvent.

The present invention uniquely features cooperative implementation of an organic solvent and an image recorder. For most embodiments of the present invention the organic solvent is effectively housed in a matrix which serves as a vehicle for delivering or "accessibilizing" the organic solvent. A matrix according to this invention operates on a principle of external accessibility to touch of the organic solvent which is contained by the matrix. The matrix may be so composed and configured as to admit of containment of an organic solvent whereby the organic solvent is accessible from without to human touch.

The matrix according to this invention is either mechanical or chemical in nature, thus operating on either of two principles of containment. Mechanical matrices function essentially by means of discernible physical containment of the solvent by one or more distinctly different materials, whereas "chemical" matrices function essentially by means of containment in the context of macroscopic homogeneity. Either principle of containment permits, upon appropriate contact by the skin area with respect to the image producer, coating of the skin area by a quantity inclusive of organic solvent.

For many mechanical matrix embodiments the matrix functions by means of "sponge-like" containment of the organic solvent by the matrix. For other mechanical matrix embodiments the matrix functions as a mere enclosure-type receptacle, e.g., a dish, which, essentially, nonporously and nonabsorently holds the organic solvent for access. For yet other mechanical matrix embodiments, the matrix functions by means of a combination of the above, e.g., a bottle with a sponge stopper cap.

For sponge-like mechanical matrix embodiments of this invention, the matrix may be made of any appropriate fibrous or porous material, natural or synthetic, which has the absorbent properties of a sponge. Most such embodiments are made of conventional sponge, foam, fabric or paper material. The matrix for such embodiments may thus be in the form of any of several commercially available products, for example, a common household sponge or foam pad, a sponge such as commonly used to moisten glue on stamps and envelopes, a fabric pad such as commonly used to ink a rubber stamp, a folded-up paper towel, a pre-moistened towlette, etc. In accordance with many such embodiments of the present invention, the matrix is a product which is obtained "dry" and then made to absorb and thereby contain the organic solvent. Some such embodiments, however, notably pre-moistened paper products, could provide both the matrix and the organic solvent physically contained by the matrix.

A matrix according to this invention operates on the principle of external accessibility to touch of the organic solvent which is contained by the matrix. The matrix may be so composed and configured as to admit of containment of an organic solvent whereby the organic solvent is accessible from without to human touch.

Although not wishing to be bound by theory, it is believed that an image producer which has a chemical matrix in accordance with the present invention may perhaps best be described as "thixotropic" or as having "thixotropic" properties. Thixotropy is a characteristic of some colloidal gels. Thixotropic materials do not readily admit of description in terms of solidity versus liquidity or in terms of viscosity, because they coagulate (i.e., become stiff and jelly-like) when at rest, and become fluid when agitated or otherwise subjected to stress. chemical matrix should have such thixotropy or thixotropic quality as to permit appropriate release of the organic solvent onto the skin area which contacts the matrix. Fingertip moistener, "solid stick" deodorant and/or antiperspirant, and lip balm were tested by the U.S. Navy; these are but examples of the various types of commercially available cosmetic, office or other products which may provide the chemical matrix and the organic solvent contained thereby in accordance with the present invention.

Accordingly, the present invention provides new and improved method and apparatus for inklessly, neatly, facilely, portably, non-toxically, economically, efficiently and effectively performing human skin printing such as fingerprinting, hand printing and infant foot printing. The integrity of the skin print which is generated in accordance with this invention is comparable to that which is generated in accordance with conventional ink skin printing technique. With the exercise of such degree and level of care and skill as are normally associated with administering conventional ink skin printing technique, a quality skin print is generated in accordance with the present invention.

When conventional pigment-type ink is used for fingerprinting, the integrity of the skin print depends upon the care and skill of the fingerprinting practitioner. A suitable quantity of wet ink is required to be placed upon the finger to impart the fingerprint. Application of too little or too much ink upon the finger may result in neglecting or obscuring some details of the fingerprint. In addition, the ink-laden finger must be deftly applied to the surface with complete steadiness and appropriate pressure. Less adroitness in applying the finger onto the surface may result in faintness, obscurity or blurring of the fingerprint due to slippage and/or excessive or insufficient pressure.

Analogous considerations pertain to practice of the present invention and practice of conventional ink fingerprinting in terms of optimizing the generated fingerprint. The fingerprint administrator for either practice similarly seeks to minimize blurring and obscuring while maximizing contrast of the image. The practitioner of the present invention seeks to appropriately coat the skin area with a suitable quantity of organic solvent-including substance and then to appropriately press the coated skin area upon the image recorder, thereby effectuating an optimum print.

The quantity of substance which includes an organic solvent has liquid properties for most embodiments; the quantity should have a suitably thick, applicable consistency, appropriate for coating the skin area to be printed. The viscosity of the quantity of substance should be high enough to prevent "running" thereof upon a skin area, but not so high as to prevent a fairly even distribution upon the skin area when coating that skin area with the quantity.

The technique for coating a skin area with conventional pigment-type ink generally involves a "rolling" motion of the subject's skin area, this "rolling" motion guided by the fingerprinting practitioner. Depending on the particular embodiment of the present invention, techniques which have been found to be preferred have involved either a "rubbing" motion, or a "tapping" motion, or a "dabbing-and-rubbing" motion, or a combination of these motions.

In tests conducted by the U.S. Navy it was found that, generally speaking, coating for mechanical matrix embodiments was preferably effectuated via either rubbing the matrix or rubbing and/or dabbing the matrix followed by rubbing the hands together. Coating for chemical matrix embodiments was preferably effectuated via either rubbing or tapping the matrix.

Other objects, advantages and features of this invention will become apparent from the following detailed description of the invention when considered in conjunction with the accompanying drawings.

BRIEF DESCRIPTION OF THE DRAWINGS

In order that the present invention may be clearly understood, it will now be described, by way of example, with reference to the accompanying drawings, wherein like numbers indicate the same or similar components, and wherein.

DETAILED DESCRIPTION OF THE INVENTION

Figure 1:
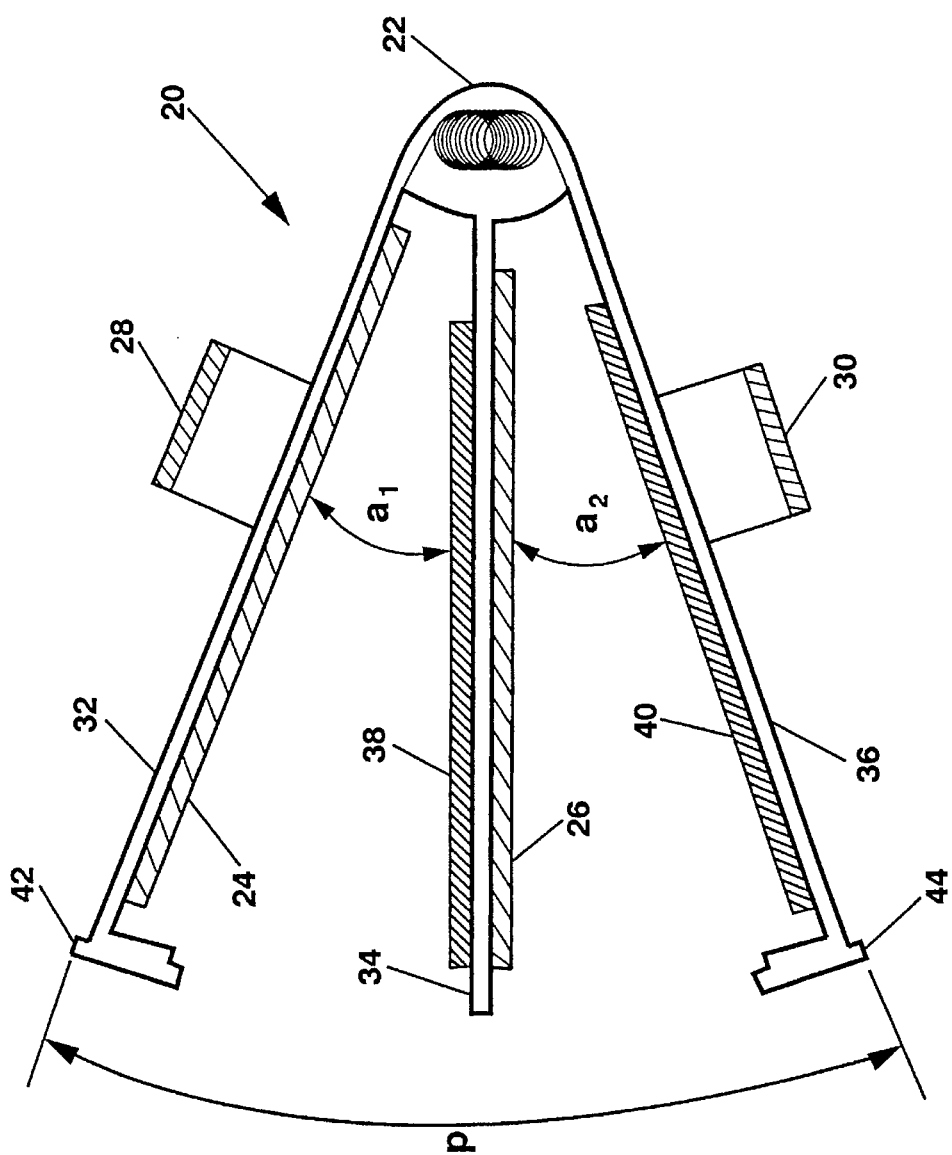
FIG. 1 is a diagrammatic side elevational view of an embodiment of a fingerprinting device in accordance with the present invention, wherein the fingerprinting device is in the "open" position.

Referring now to FIG. 1, fingerprinting device 20 is planarly-angularly pivotable about a flexible or jointed hinge such as symbolically represented flexible spring hinge 22. Upper foam layer 24 and middle foam layer 26 are for providing buffering for the fingerprinted subject's hand during operation of fingerprinting device 20. Upper hand strap 28 and lower hand strap 30 are for securing the fingerprinting practitioner's grip while grasping fingerprinting device 20.

Fingerprinting device 20 has three sections, viz., sections 32, 34 and 36, which are joined at hinge 22. Upper hand strap 28 is attached to upper section 32 of fingerprinting device 20 and lower hand strap 30 is attached to lower section 36 of fingerprinting device 20. Upper section 32 includes, at its bottom surface, upper foam layer 24. Middle section 34 includes, at its top surface, image producer 38 and, at its bottom surface, middle foam layer 26. Lower section 36 includes, at its top surface, image recorder 40.

Fingerprinting device 20 is pivotably "openable" and "closeable" as indicated by bi-directional arc p. Image producer 38 and image recorder 40 are accessible for contact by the fingerprinted subject's skin while fingerprinting device 20 is recoiled in the open position.

Figure 2:
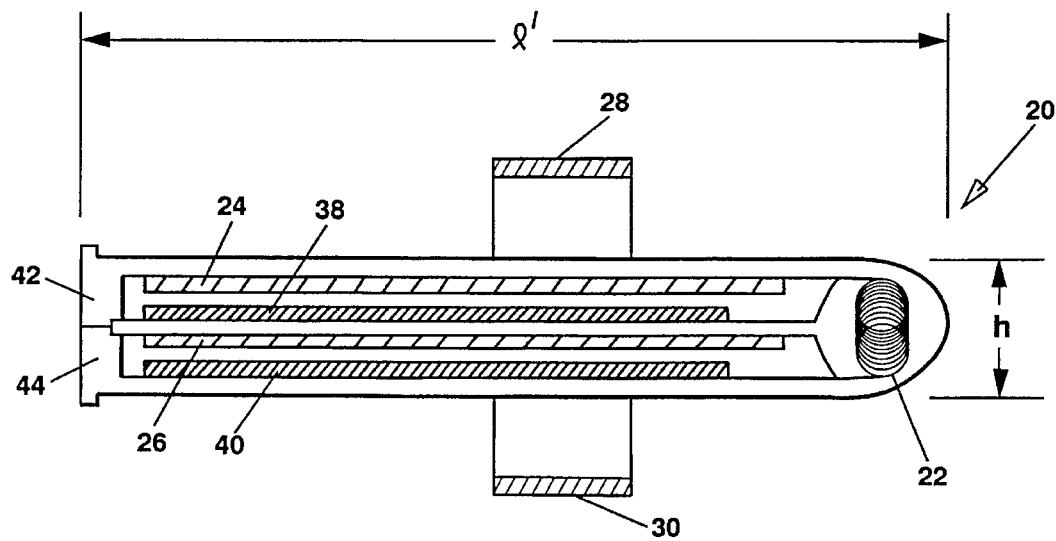
FIG. 2 is a diagrammatic side elevational view of the embodiment shown in FIG. 1, wherein the fingerprinting device is in the "closed" position.
Figure 3:
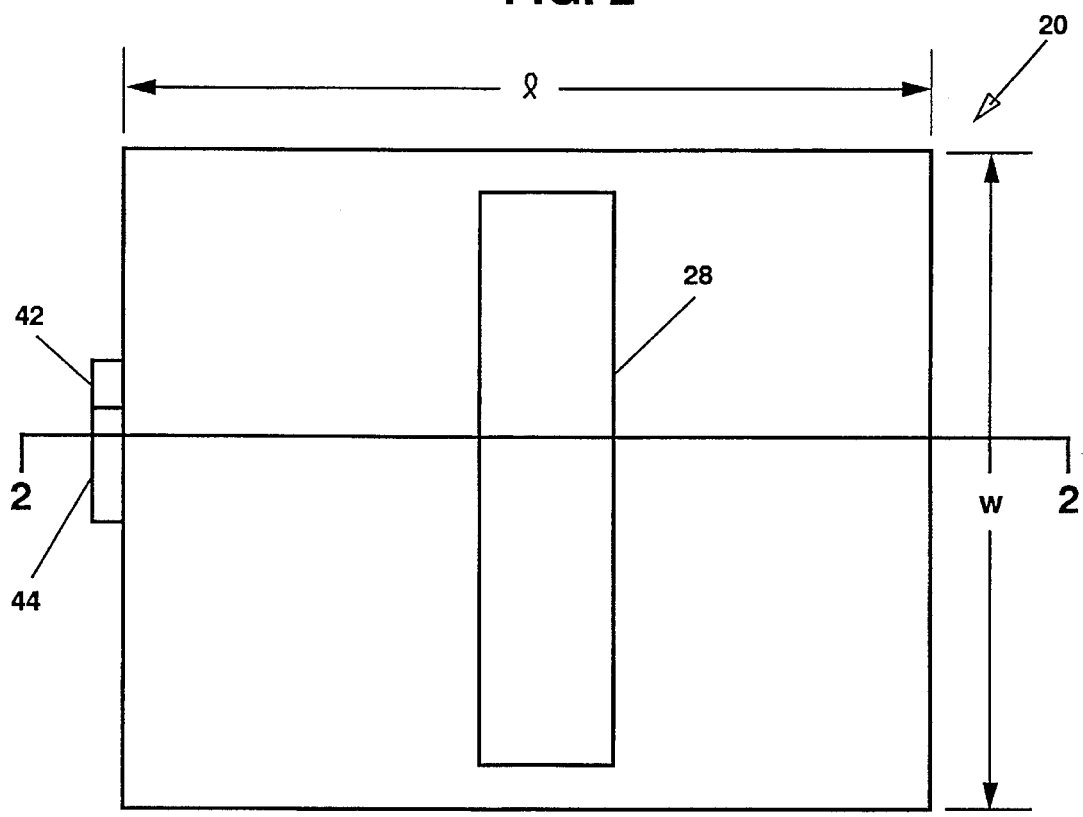
FIG. 3 is a diagrammatic top plan view of the embodiment shown in FIG. 1, wherein the fingerprinting device is in the "closed" position.

With reference to FIG. 2 and FIG. 3, upper snap element 42 and lower snap element 44 engage to fasten fingerprinting device 20 in the closed position. Approximate preferred dimensions for fingerprinting device 20 are length 1 (or length 1', which includes protrusion of snap elements 42 and 44) equal to five inches, width w equal to six inches, height h equal to two to three inches, and open position arc p, shown in FIG. 1, equal to ninety degrees.

Figure 4:
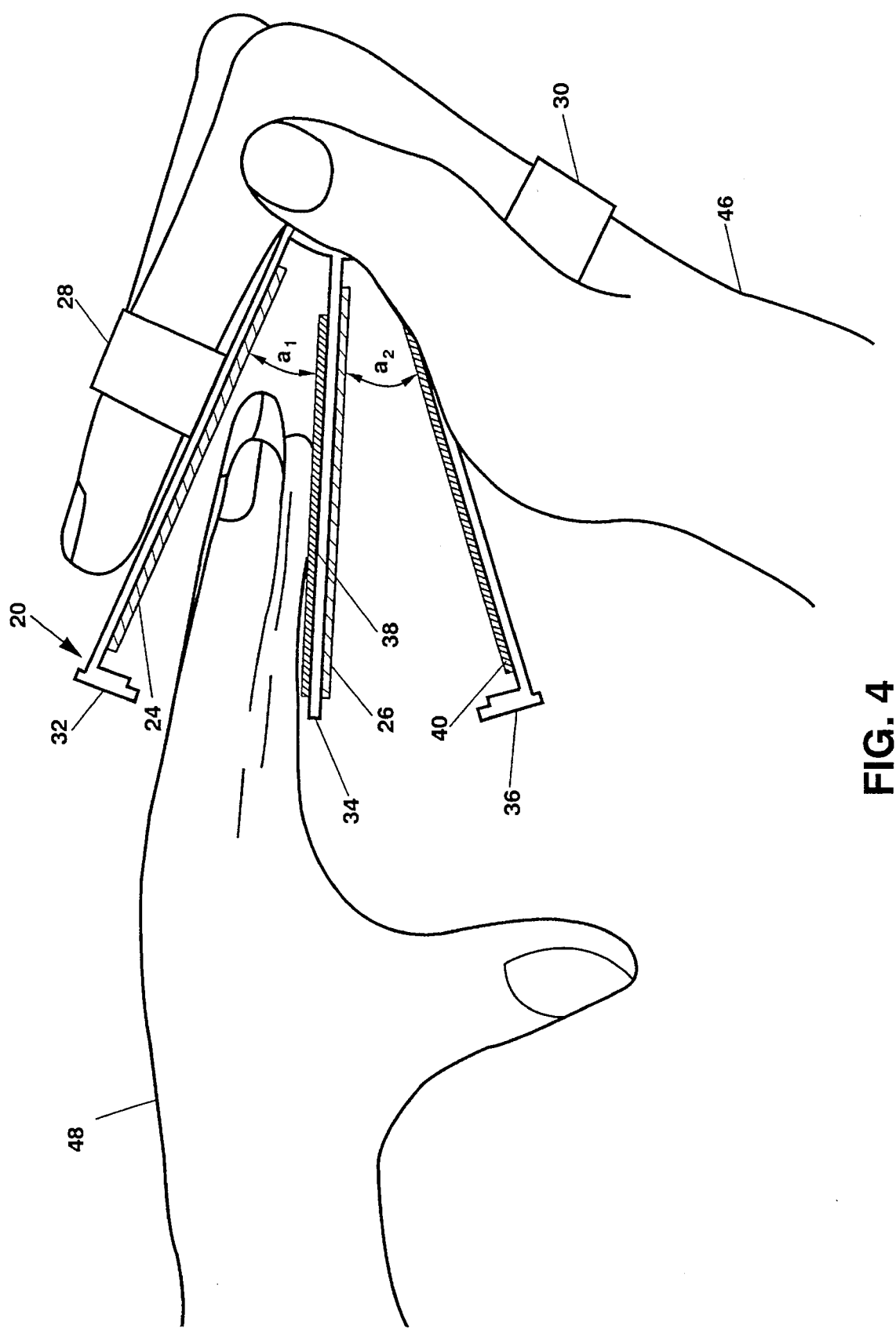
FIG. 4 is a diagrammatic side elevational view of the embodiment shown in FIG. 1, wherein the fingerprinting device is in the "open" position and in operation.

Reference now being made to FIG. 4, fingerprinting device 20 is hand-held by the fingerprinting practitioner. Fingerprinting device 20 is grasped by practitioner's hand 46, secured by upper hand strap 28 and lower hand strap 30, for purposes of obtaining fingerprints from fingerprinted subject's hand 48. Upper foam layer 24 and lower foam layer 26, respectively, provide protective padding while subject's hand 48 contacts image producer 38 and image recorder 40, respectively. Hinge 22 is of such complexity as to result in approximate equality of angles $a_1$ and $a_2$ for all values of $a_1$ and $a_2$.

Fingerprinting device 20 is recoiled in the open position while being held and perhaps slightly compressed by practitioner's hand 46, this compression perhaps to some extent depending on the size of subject's hand 48. Upper hand strap 28 secures three or four fingers of practitioner's hand 46 while lower hand strap 30 secures the palm area of practitioner's hand 46. Based on this hand-held configuration, during operation of fingerprinting device 20 subject's hand 48 is preferably held in a substantially vertical position, with fingers up and palm out for fingerprints, as shown in FIG. 5, and with fingers clenched or bent into a fist and thumb up for thumbprints, as shown in FIG. 6.

Referring again to FIG. 4, other hand-held configurations are possible in practicing the present invention. For example, for some embodiments of fingerprinting device 20, upper hand strap 28 may be used to secure three or four fingers of practitioner's hand 46 while lower hand strap 30 secures the thumb area of practitioner's hand 46. This hand-held configuration may facilitate maneuverability of practitioner's hand 46 and thereby lend itself to operation of fingerprinting device 20 wherein subject's hand 48 is held not only in a vertical position but also at a variety of angles, including in a horizontal position.

The angle of subject's hand 48 during operation of fingerprinting device 20 is important primarily insofar as it affects the comfort and finesse of the practitioner while grasping fingerprinting device 20. The relative disposition of practitioner's hand 46 with respect to subject's hand 48 should be such as to permit optimal effectuation of the practitioner's fingerprinting technique in accordance with the present invention.

Figure 5:
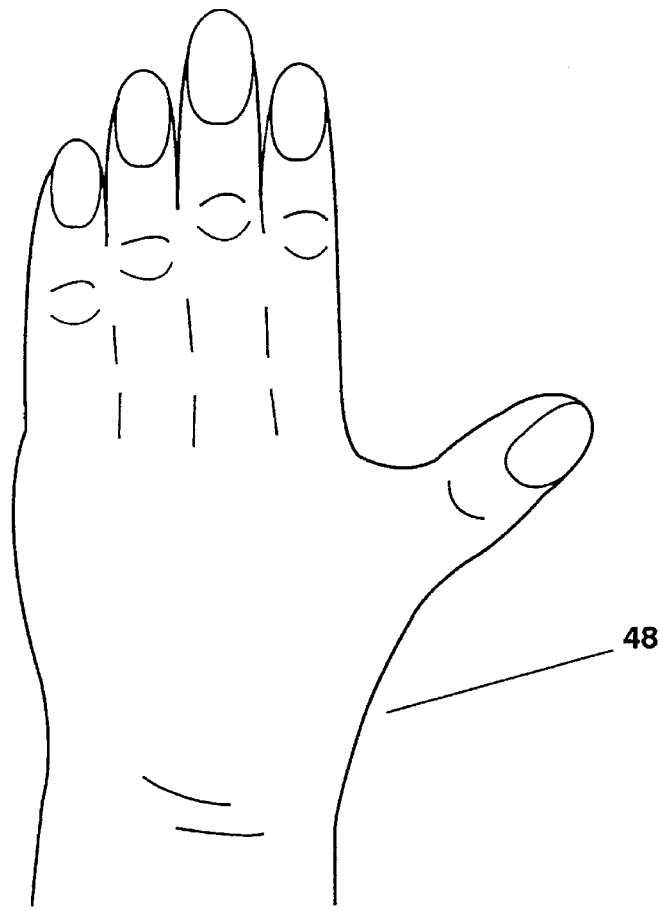
FIG. 5 and FIG. 6 are diagrammatic perspective views illustrating positions of a human hand from which fingerprints are to be taken.
Figure 6:
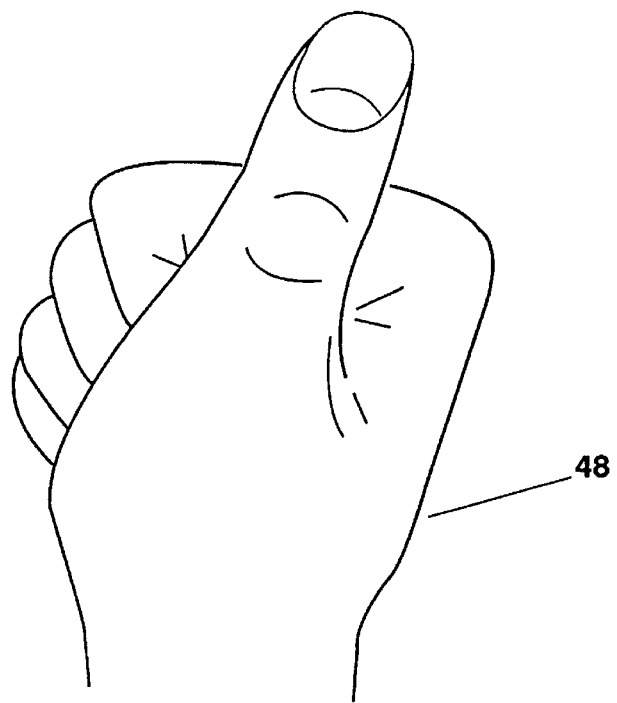

Still referring to FIG. 4, in operation of this embodiment of the present invention, the subject first holds subject's hand 48 vertically stationary as shown in FIG. 5. While grasping fingerprinting device 20, the practitioner positions practitioner's hand 46 whereby the four fingers of subject's hand 48 are situated between the bottom surface of upper section 32 and the top surface of middle section 34, and whereby said 15. subject's fingers are situated proximate and generally parallel with respect to image producer 38, approximately as illustrated in FIG. 4. The practitioner at this point closes and opens fingerprinting device 20 with the appropriate technique for optimizing effectuation of the coating step.

The appropriate coating technique is "tapping" for an image producer 38 having a chemical matrix characteristic of that of fingertip moisteners such as were tested by the U.S. Navy. Practitioner's hand 46 makes a rapid closing-and-opening motion so as to momentarily decrease and then immediate increase the angle $a_1$ between upper section 32 and middle section 34, thereby effectuating a single "tap." The practitioner then withdraws fingerprinting device 20 from subject's hand 48.

The appropriate coating technique may be "rubbing" for some image producers 38 having a chemical matrix characteristic of that of stick deodorants and/or antiperspirants such as were tested by the U.S. Navy. The appropriate technique may also be "rubbing" for an image producer 38 having a mechanical matrix characteristic of foams, sponges and fabric rubber stamp pads such as were tested by the U.S. Navy.

In order to effectuate "rubbing," practitioner's hand 46 makes a closing motion so as to momentarily decrease angle $a_1$ and causes the finger skin areas of subject's hand 48 to rubbingly contact image producer 38 while practitioner's hand withdraws fingerprinting device 20 from subject's hand 48. Alternatively, "rubbing" may preferably be accomplished by using the "tapping" technique followed by having the subject rub both of subject's hands 48 together.

The distal phalanx skin areas of the four fingers of subject's hand 48 have thus appropriately tapped or rubbed image producer 38 and thereby been appropriately coated with organic solvent from image producer 38. Within a few seconds, while subject's hand 48 is held vertically motionless and the practitioner continues to grasp fingerprinting device 20, the practitioner positions practitioner's hand 46 whereby the four fingers of subject's hand 48 are situated between the bottom surface of middle section 34 and the top surface of bottom section 36, and whereby said subject's fingers are situated proximate and generally parallel with respect to image recorder 40. Practitioner's hand 46 then makes a closing-and-opening motion so as to momentarily decrease and then immediately increase the angle $a_2$ between middle section 34 and lower section 36. The practitioner then again withdraws fingerprinting device 20 from subject's hand 48.

The preferred duration of this-closing-and-opening motion for purposes of impressing depends on the embodiment and should not exceed a few seconds for most embodiments. Longer duration contact may serve to enhance the impression, due to more complete absorption from the finger skin areas to the image recorder of the quantity of substance or of the organic solvent, and/or due to the transmission of the subject's body heat through the finger skin areas. On the other hand, longer duration contact may be counterproductive as increasing the likelihood of image distortion. The coated skin areas of the four fingers of subject's hand 48 have thus appropriately contacted image recorder 40 and have thereby appropriately impressed four images corresponding to the coated skin areas upon image recorder 40.

The above-described coating and imaging steps may be essentially repeated for taking thumbprints of subject's hand 48. The subject first holds subject's hand 48 vertically stationary as shown in FIG. 6. While grasping fingerprinting device 20, the practitioner positions practitioner's hand 46 whereby the thumb of subject's hand 48 is situated between the bottom surface of upper section 32 and the top surface of middle section 34, and whereby said subject's thumb is situated proximate and generally parallel with respect to image producer 38. Practitioner's hand 46 then makes a rapid closing-and-opening motion so as to momentarily decrease and then immediate increase the angle $a_1$ between upper section 32 and middle section 34; the practitioner then withdraws fingerprinting device 20 from subject's hand 48. For some such embodiments the subject is immediately directed to appropriately rub subject's hands 48 together. Alternatively, practitioner's hand 46 makes a closing motion so as to momentarily decrease angle $a_1$ and causes the thumb skin area of subject's hand 48 to rubbingly contact image producer 38 while practitioner's hand withdraws fingerprinting device 20 from subject's hand 48. The distal phalanx skin area of subject's thumb has thus appropriately tapped or rubbed image producer 38 and thereby been appropriately coated with organic solvent from image producer 38.

Within a few seconds, while subject's hand 48 is held vertically motionless and the practitioner continues to grasp fingerprinting device 20, the practitioner positions practitioner's hand 46 whereby the thumb of subject's hand 48 is situated between the bottom surface of middle section 34 and the top surface of bottom section 36, and whereby said subject's thumb is situated proximate and generally parallel with respect to image recorder 40. Practitioner's hand 46 then makes a closing-and-opening motion so as to momentarily decrease and then immediately increase the angle $a_2$ between middle section 34 and lower section 36. The practitioner then again withdraws fingerprinting device 20 from subject's hand 48. The coated skin area of subject's thumb has thus appropriately contacted image recorder 40 and has thereby appropriately impressed an image corresponding to the coated skin area upon image recorder 40.

Once the corresponding coated skin area has been withdrawn from image recorder 40, an impression is immediately or imminently appreciable. Depending upon the embodiment, the impression visibly formed upon image recorder 40 will initially be slightly to moderately visible. Over an ensuing period of time generally not exceeding about ten minutes, the duration of which depends upon the embodiment of the present invention and perhaps the environment in which it is practiced, the impression appreciably develops and finally matures into the full-fledged generated fingerprint.

Figure 7:
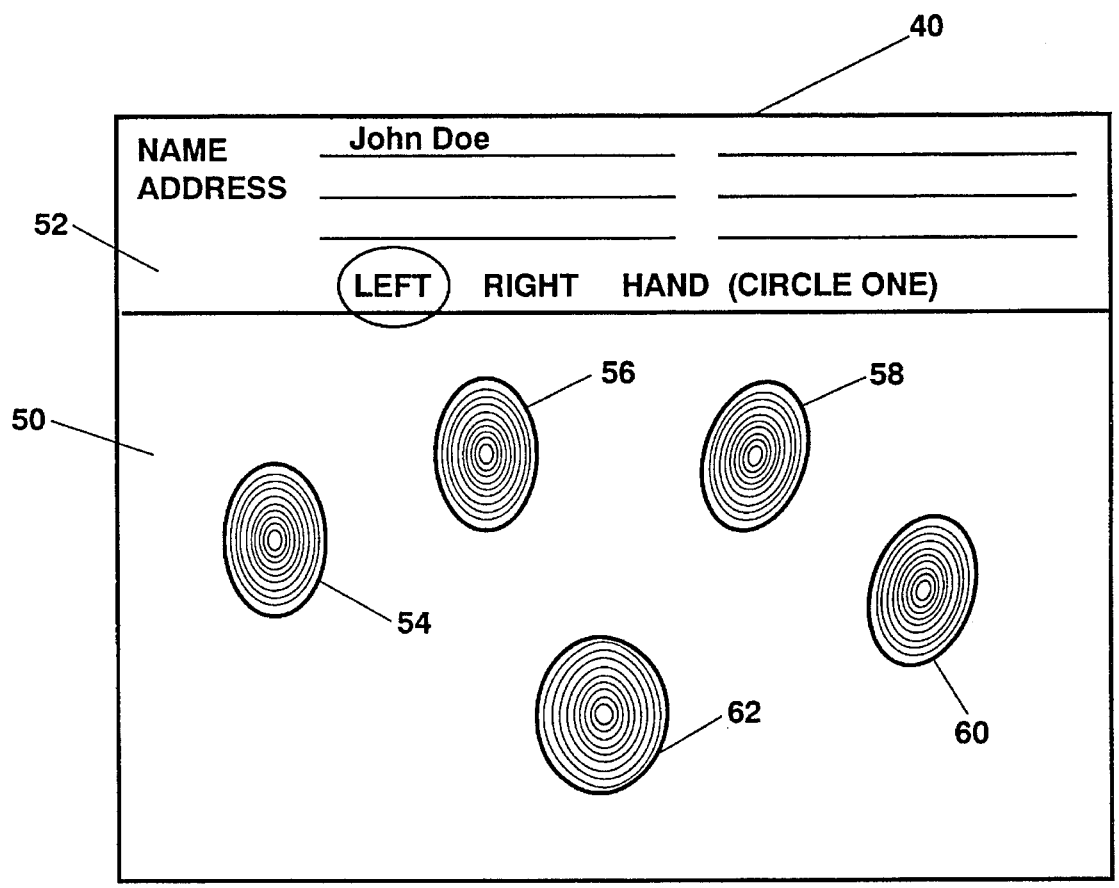
FIG. 7 is a diagrammatic top plan view of an embodiment of an image recorder card in accordance with the present invention.

For some embodiments image recorder 40 is, or is made a part of, a standard form whereupon fingerprints may be taken and information may be written. Now referring to FIG. 7, image recorder card 40 has a lower portion 50 which includes a fingerprinting surface and an upper portion 52 which includes a writing surface. The entire image recorder card 40 has a thin cardboard consistency or backing. Lower portion 50 surfacially has a thermal paper material, and upper portion 52 surfacially has a "plain" paper material which facilitates legible writing thereon of relevant information. For utilization with the embodiment shown in FIG. 1, for example, image recorder card 40 may be envisioned as preferably placed with upper portion 52 at the inside of fingerprinting device 20, widthwise adjacent to and parallel with hinge 22. Representatively illustrated in FIG. 7 are subject's left hand 48 fingerprints, fully developed, which have been generated in accordance with the present invention, viz., little fingerprint 54, ring fingerprint 56, middle fingerprint 58, index fingerprint 60 and thumbprint 62.

Once full maturation has been reached, the fingerprints may be photocopied. For some applications photocopying, such as by means of xerography, may serve some beneficial purposes. Photocopying may provide additional and/or enlarged renditions of the original fingerprints in furtherance of recordkeeping. Englargment of a fingerprint may also serve to enhance appreciation of its detail. Moreover, conventional xerographic copying often serves to enhance the contrast of the original image and may thus actually provide an improved rendition of an original fingerprint. Furthermore, a photocopied rendition is generally more robust and chemically resistent than an original thermal paper rendition; the photocopy is less susceptible to unwanted mechanical or chemical alteration.

After the coated skin area has been withdrawn from image recorder 40, for some embodiments it may be preferable that heat be applied to image recorder 40, more specifically to the developing impression in image recorder 40. Heat application may serve to directly chemically enhance the color-producing interaction of the electron-donating chromogenic composition and the electron-accepting composition, and/or may serve to indirectly enhance this interaction by promoting or furthering the breakdown of the binder in the image recorder. For other embodiments, heat application to the image recorder may preferably commence prior to effectuating the impressing step so that image recorder 40 reaches or approaches a desired temperature for purposes of enhancing development of the impression.

Figure 8:
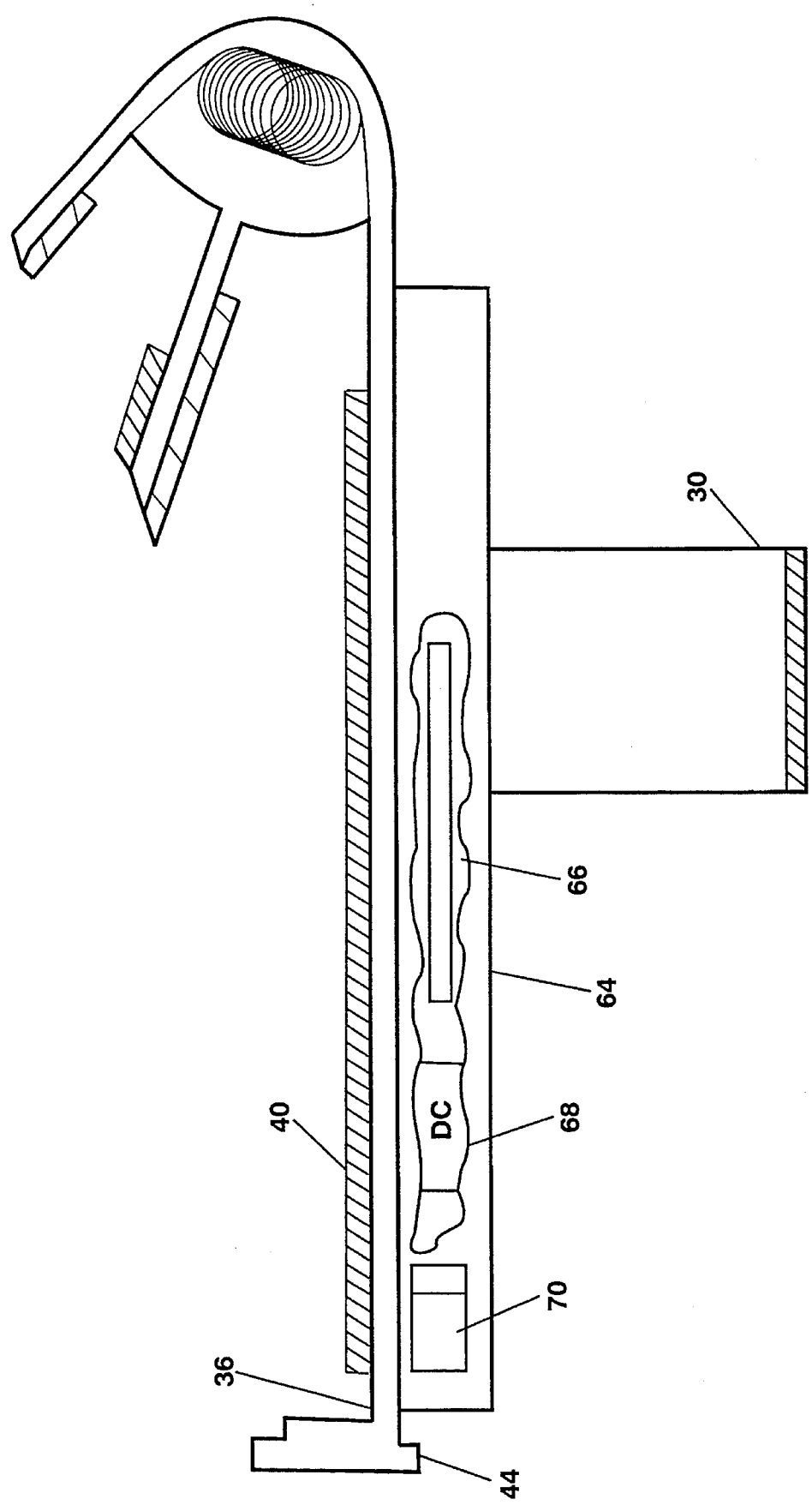
FIG. 8 is an enlarged partial view of an embodiment such as that shown in FIG. 1 which includes a heater.

Referring to FIG. 8, lower section 36 incorporates battery-powered heater 64 so as to essentially constitute a "hot plate." Heater 64 includes heating element 66, dc power supply 68 and actuation mechanism 70. Power supply 68 provides the electric current which heats element 66 as well as powers actuation mechanism 70. Mechanism 70 may include, for example, one or more switches of a rocker, sliding, push-button and/or dial type, and may provide on-off function and/or automatic timing function. Mechanism 70 may be activated prior to, during or subsequent to effectuation of the impressing step. For automatically timed heat, the heat may be activated for an individually set duration and/or may be activated for a predeterminedly set duration. Alternatively, mechanism 70 may be an unpowered on/off switch, spring-loaded so as to effect an automatic timed function.

For most embodiments the heat should be applied so as to render the thermal paper material of image recorder 40 at a temperature of approximately 100° F, and for most embodiments should be applied for a duration of no less than one second and no greater than one minute. Optimization of heat application depends on the particular embodiment of the present invention, and it is well within the capability of the ordinarily skilled artisan in practice to determine such optimization. For some embodiments of the present invention, heat may be externally applied to the developing impression by, for example, a heat lamp, an incandescent lamp, a hair dryer, a heat gun or a hot plate. With regard to quality optimization of the print, the particular means for applying heat is not important so much as the amount of heat energy which is actually brought to bear upon the developing impression.

Figure 9:
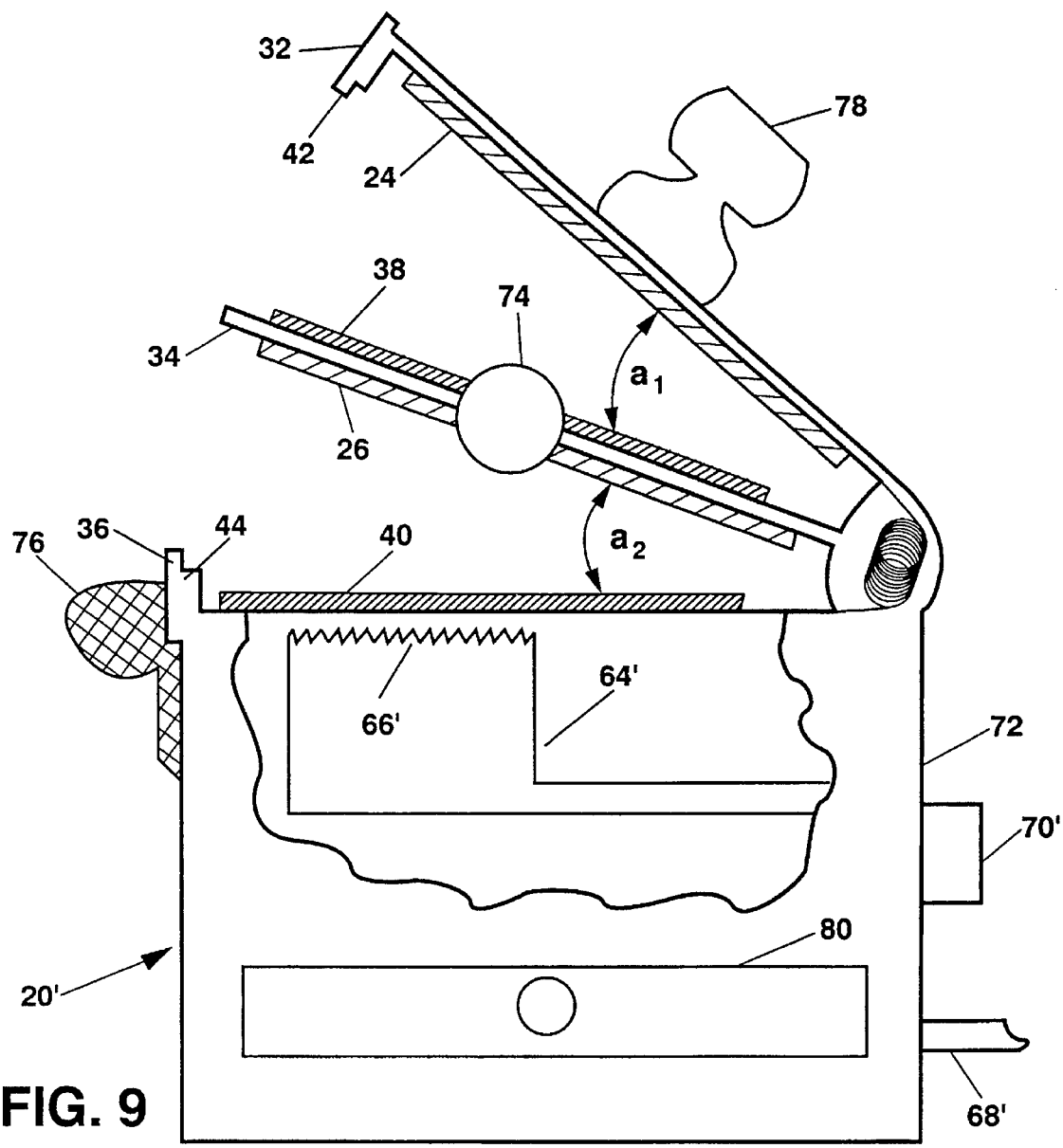
FIG. 9 is a diagrammatic side elevational view of another embodiment of a fingerprinting device in accordance with the present invention, wherein the fingerprinting device is in the "open" position, with a portion cut away to show some interior detail.
Figure 10:
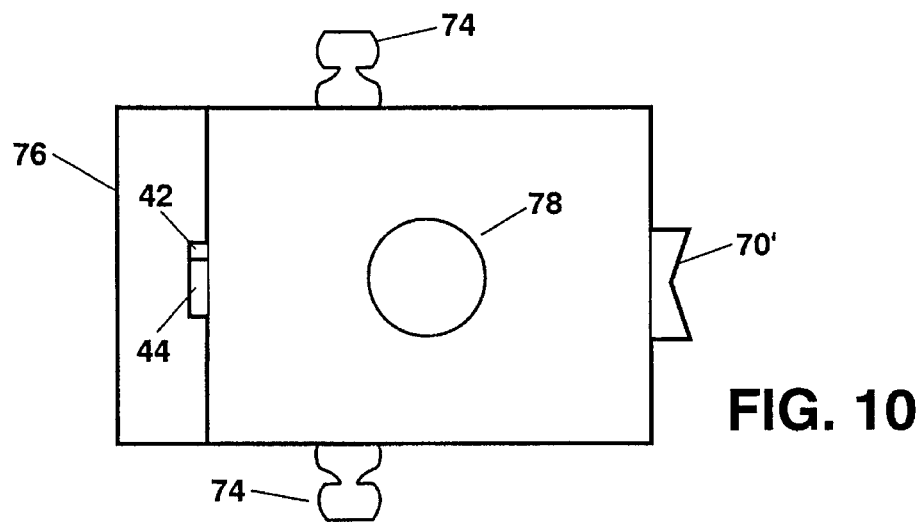
FIG. 10 is a diagrammatic top plan view of the embodiment shown in FIG. 9, wherein the fingerprinting device is in the "closed" position.

A similar embodiment of the present invention may be styled an "office model" as distinguished from a "portable model" such as discussed hereinabove. Reference now being made to FIG. 9 and FIG. 10, fingerprinting device 20' is essentially fingerprinting device 20 coupled with base 72.

In operation of this embodiment intended for stationary use, the practitioner grasps side handle 74 with right practitioner's hand 46 so as to downwardly rotate middle section 34 until angle $a_2$ is zero. The bottom surface of middle section 34 and the top surface of lower section 36 are thus maintained approximately parallel and noncontiguously adjacent by practitioner's continued grasp of side handle 74. The subject holds subject's hand 48 horizontally stationary with fingers readied as shown in FIG. 5. The practitioner manually guides and positions the four fingers of subject's hand 48 between the bottom surface of upper section 32 and the top surface of middle section 34, whereby said subject's fingers are situated proximately and generally parallel with respect to image producer 38. The palm of subject's hand 48 rests comfortably on hand-rest extension 76. Practitioner's hand 46 then exerts a rapid downward force upon press button 78 so as to momentarily decrease the angle $a_1$ between upper section 32 and middle section 34; the practitioner then withdraws subject's hand 48 from fingerprinting device 20'. For some such embodiments the subject is immediately directed to appropriately rub subject's hands 48 together. Alternatively, practitioner's hand 46 makes a closing motion so as to momentarily decrease angle $a_1$ and causes the finger skin areas of subject's hand 48 to rubbingly contact image producer 38 while practitioner's hand causes subject's hand 48 to withdraw from fingerprinting device 20'. The distal phalanx skin areas of the four fingers of subject's hand 48 have thus appropriately tapped or rubbed image producer 38 and thereby been appropriately coated by organic solvent from image producer 38.

The practitioner then releases side handle 74 so as to permit middle section 34 to recoilingly rotate upward and equilibrate into motionlessness. The practitioner grasps side handle 74 and top section 32 with right practitioner's hand 46 so as to upwardly rotate middle section 34 until angle $a_1$ is zero. the top surface of middle section 34 and the bottom surface of upper section 32 are thus maintained approximately parallel and noncontiguously adjacent by practitioner's continued grasp of side handle 74 and top section 32. The practitioner manually repositions subject's hand 48 whereby the four fingers of subject's hand 48 are situated between the bottom surface of middle section 34 and the top surface of bottom section 36, and whereby said subject's four fingers are situated proximate and generally parallel with respect to image recorder 40. The palm of subject's hand 48 rests comfortably on hand-rest extension 76. Practitioner's hand 46 then exerts a downward force upon press button 78 so as to momentarily decrease the angle $a_2$ between middle section 34 and lower section 36; the practitioner then again withdraws subject's hand 48 from fingerprinting device 20'. The coated skin areas of the four fingers of subject's hand 48 have thus appropriately contacted image recorder 40 and have thereby appropriately impressed four images corresponding to the coated skin areas upon image recorder 40.

Still referring to FIG. 9 and FIG. 10, the above-described coating and imaging steps may be essentially repeated for taking thumbprints of subject's hand 48. The practitioner grasps side handle 74 with right practitioner's hand 46 so as to downwardly rotate middle section 34 until angle $a_2$ is zero. The bottom surface of middle section 34 and the top surface of lower section 36 are thus maintained approximately parallel and noncontiguously adjacent by practitioner's continued grasp of side handle 74. The subject holds subject's hand 48 horizontally stationary with thumb readied as shown in FIG. 6. The practitioner manually guides and positions the thumb of subject's hand 48 between the bottom surface of upper section 32 and the top surface of middle section 34, whereby said subject's thumb is situated proximate and generally parallel with respect to image producer 38. The bent fingers of subject's hand 48 comfortably grasp hand-rest extension 76. Practitioner's hand 46 then exerts a rapid downward force upon press button 78 so as to momentarily decrease the angle $a_1$ between upper section 32 and middle section 34; the practitioner then withdraws subject's hand 48 from fingerprinting device 20'. For some such embodiments the subject is immediately directed to appropriately rub subject's hands 48 together. Alternatively, practitioner's hand 46 makes a closing motion so as to momentarily decrease angle $a_1$ and causes the thumb skin area of subject's hand 48 to rubbingly contact image producer 38 while practitioner's hand causes subject's hand 48 to withdraw from fingerprinting device 20'. The distal phalanx skin area of the thumb of subject's hand 48 has thus appropriately tapped or rubbed image producer 38 and thereby been appropriately coated by organic solvent from image producer 38.

The practitioner then releases side handle 74 so as to permit middle section 34 to recoilingly rotate upward and equilibrate into motionlessness. The practitioner grasps side handle 74 and top section 32 with right practitioner's hand 46 so as to upwardly rotate middle section 34 until angle $a_1$ is zero. The top surface of middle section 34 and the bottom surface of upper section 32 are thus maintained approximately parallel and noncontiguously adjacent by practitioner's continued grasp of side handle 74 and top section 32. The practitioner manually repositions subject's hand 48 whereby the thumb of subject's hand 38 is situated between the bottom surface of middle section 34 and the top surface of bottom section 36, and whereby said subject's thumb is situated proximately and generally parallel with respect to image recorder 40. The bent fingers of subject's hand 48 comfortably grasp hand-rest extension 76. Practitioner's hand 46 then exerts a downward force upon press button 78 so as to momentarily decrease the angle $a_2$ between middle section 34 and lower section 36; the practitioner then again withdraws subject's hand 48 from fingerprinting device 20'. The coated skin area of the thumb of subject's hand 48 has thus appropriately contacted image recorder 40 and has thereby appropriately impressed an image corresponding to the coated skin area upon image recorder 40.

With reference to FIG. 9 and FIG. 10, base 72 shown in FIG. 9 incorporates ac line-powered heater 64', which includes heating element 66', ac line 68' and actuation mechanism 70'. In this example heating element 66' represents a heating element similar to that of a conventional bread toaster. Line 68' conducts power to base 72 from an ac electrical outlet. Like mechanism 70 in FIG. 8, mechanism 70' in FIG. 9 and FIG. 10 is an appropriate type of on-off and/or timing mechanism. For some embodiments, drawer 80 provides convenient storage for blank image recorder cards 40 and/or other items.

Figure 11:
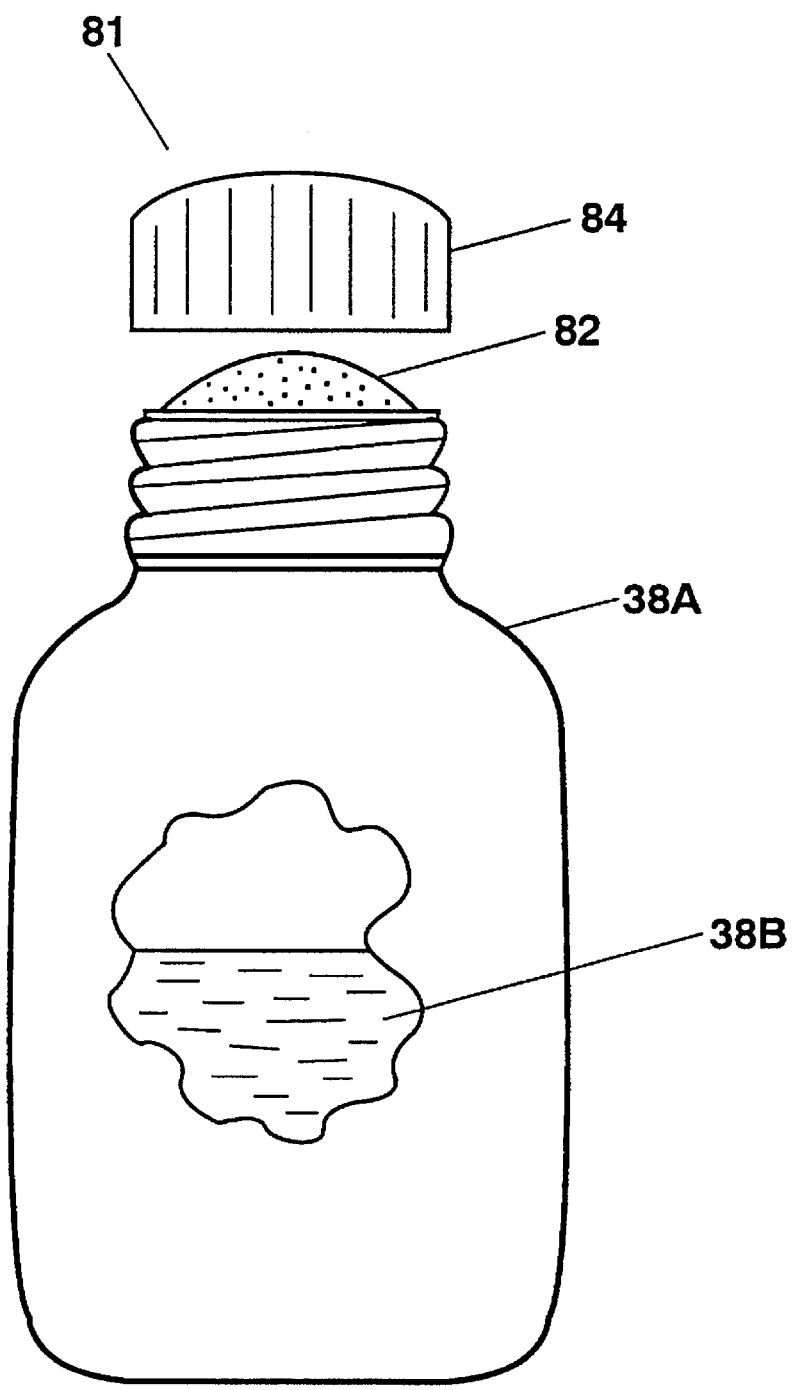
FIG. 11 is a diagrammatic elevational view of another embodiment of a fingerprinting device in accordance with the present invention, with a portion cut away to show some interior detail.

Referring to FIG. 11, many preferred embodiments of the present invention include a plastic bottle 38a having spongelike porous foam stopper 82, similar to a shoe polish bottle. This combination of bottle 38a and stopper 82 serves as the matrix for containing and delivering organic liquid solvent 38b. Plastic cap 84 may be used to seal the contents of plastic bottle 38a. The palm of the subject's hand 48 is dabbed with stopper 82, subject's hands 48 are rubbed together, and the to-be-printed skin area or areas of subject's hand 48 are pressed onto an image recorder such as shown in FIG. 7.

One such embodiment of this invention which is particularly preferred utilizes propylene glycol as liquid solvent 38b which is contained and delivered by plastic bottle 38a and foam stopper 82. The propylene glycol is preferably applied: by dabbing and rubbing; or, by dabbing and rubbing, then wiping and rubbing. The skin areas are then preferably pressed or rolled on an image recorder which is coupled with a heated clipboard.

It was found during development of the present invention that dabbing the palm of subject's hand with a foam pad soaked with propylene glycol, resulting in a wet spot on the palm, and subsequently rubbing the hands together so as to distribute the propylene glycol to the finger and thumb tips, provided an effective way of properly coating the skin for high quality prints. According to one form of this technique, the subject's hand is moistened with any appropriate solvent source, and this is followed by the subject's rubbing his or her hands together to attain proper solvent distribution and moisture level. Dabbing a wet spot and rubbing hands together, i.e., "dabbing-and-rubbing," is the preferred technique for coating the skin area or skin areas when using a mechanical matrix which comprises a plastic bottle capped with a sponge or other porous material stopper and which contains propylene glycol.

It was also demonstrated that the "dabbing-and-rubbing" could be performed by a practitioner who dabs and subsequently rubs the skin area or areas of a subject to be printed; this "practitioner-active" form of the "dabbing-and-rubbing" technique presents a highly effective approach for generating infant footprints and in other scenarios wherein "dabbing-and-rubbing" by the practitioner is advantageous.

Referring again to FIGS. 1–4 and 8–10, for embodiments involving coating the skin by means other than as represented in these figures, middle section 34 and the corresponding coating procedures utilizing middle section 34 can be eliminated. For example, plastic bottle 38a capped with sponge-like stopper 82 and containing liquid organic solvent 38b, shown in FIG. 11, can be effectively combined with a variation of the portable fingerprinting device 20 embodiment which is a bi-sectional configuration wherein there is just an upper section 32 and a lower section 36 but no middle section 34.

Figure 12:
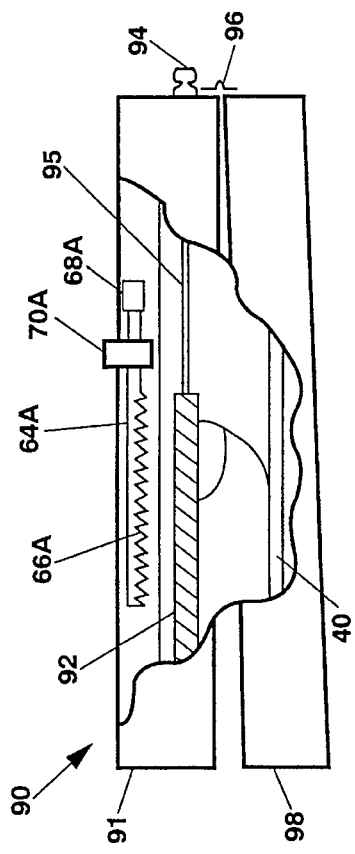
FIG. 12 is a diagrammatic elevational view of another embodiment of a fingerprinting device in accordance with the present invention, with a portion cut away to show some interior detail.
Figure 13:
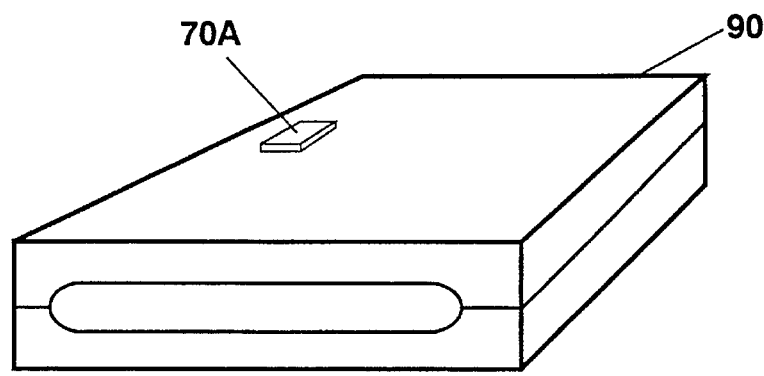
FIG. 13 is a diagrammatic perspective view of the embodiment shown in FIG. 12.

FIG. 12 and FIG. 13 show a "print-only" device according to this invention. In top section 91, device 90 has heater 64a, dc power supply 68a and actuation mechanism 70a. The practitioner opens device 90, thereby separating top section 91 from bottom section 98 via rotation around spring-loaded hinge 96, which tends to keep device 90 in the open position. The subject's fingers and thumb having each been properly coated with solvent-including substance, the practitioner records the subject's finger and thumb prints in a manner similar to that described above for operation of devices 20 and 20'. The practitioner opens device 90, removes the subject's fingers/thumbs from device 90, closes device 90, and displaces cushion 92 by pulling pull rod 95 using pull knob 94, thereby exposing image recorder 40 to heating element 66a of heater 64a. The practitioner starts heating of image recorder 40 by activating timed actuation mechanism 70a.

Figure 14:
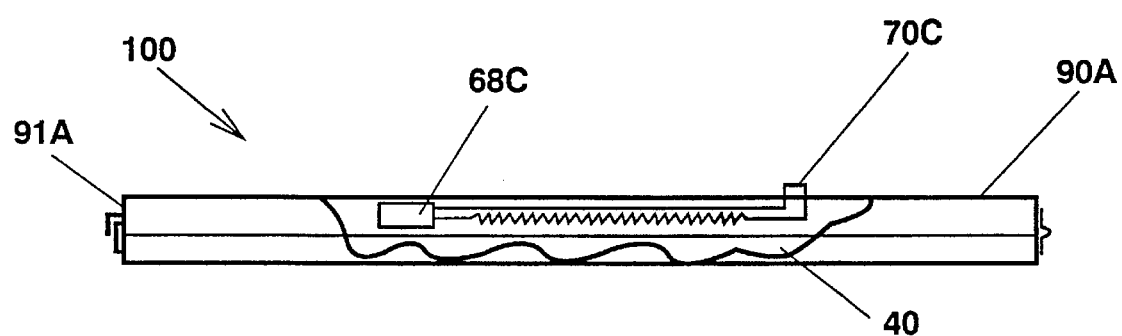
FIG. 14 is a diagrammatic elevational view of of another embodiment of a fingerprinting device in accordance with the present invention, with a portion cut away to show some interior detail.

Device 100 shown in FIG. 14 may be styled a "heated clipboard" in that it holds the image recorder 40 cards and has a heater in top section 91a. The subject's fingers and thumb having each been properly coated with solvent-including substance, with top section 91a open the fingers/thumb are pressed or rolled onto image recorder 40 by either the subject or the practitioner. The practitioner removes the subject's fingers/thumb from device 100, closes top section 91a, and commences the heating cycle by activating timed actuation mechanism 70c.

Figure 15:
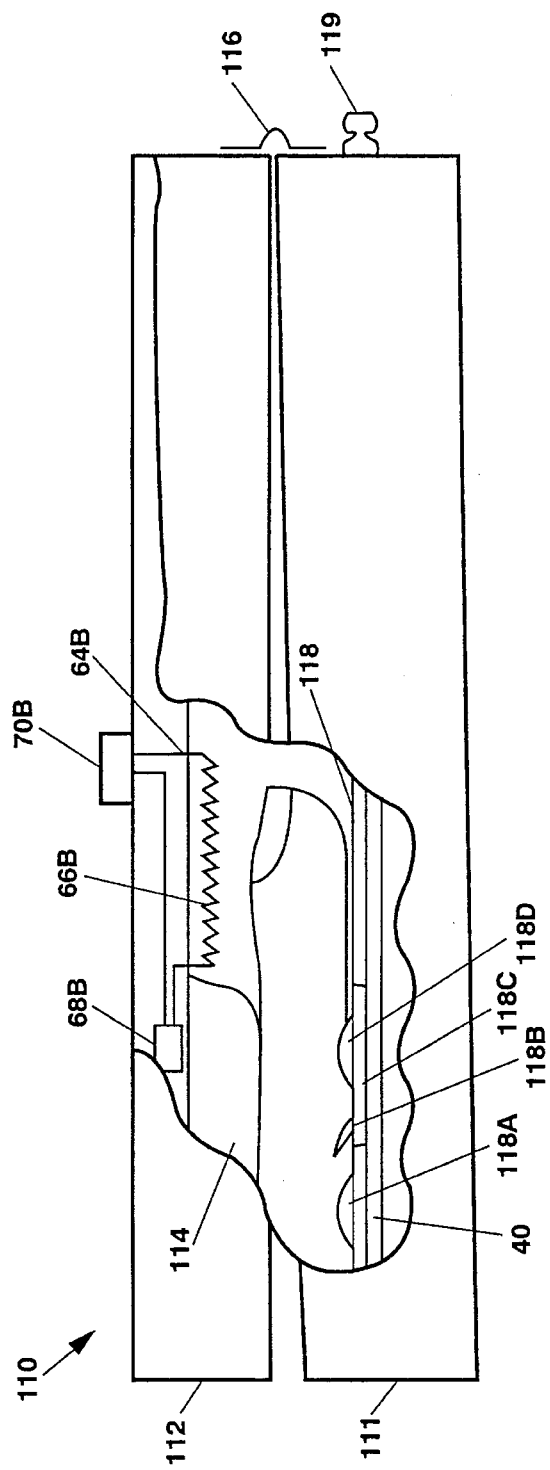
FIG. 15 is a diagrammatic elevational view of of another embodiment of a fingerprinting device in accordance with the present invention, with a portion cut away to show some interior detail.
Figure 16:
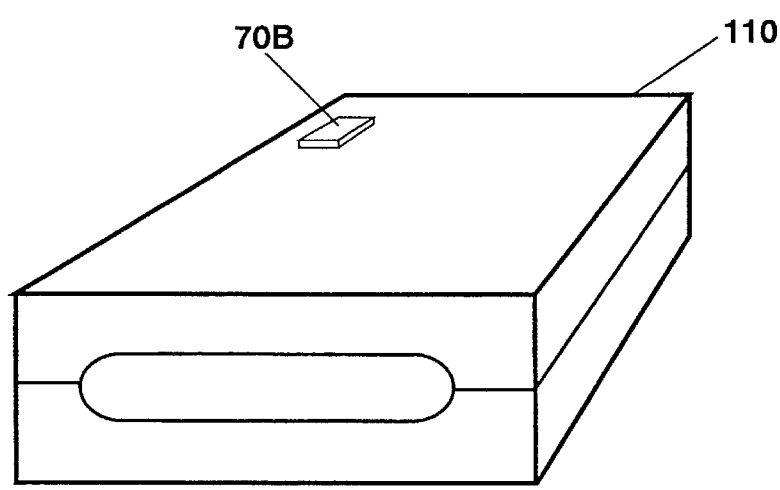
FIG. 16 is a diagrammatic perspective view of the embodiment shown in FIG. 15.

With reference to FIG. 15 and FIG. 16, device 110 may be used to generate fingerprints using a mechanical matrix containing a solvent-including substance which is liquid. Device 110 is operated in accordance with principles and skills similar to those brought to bear for operation of device 90 shown in FIG. 12 and FIG. 13. The practitioner opens device 110 by separating top section 112 from bottom section 111 via rotation around spring loaded hinge 116, which tends to keep device 110 in the open position. The practitioner positions the subject's fingers/thumb in device 110 and closes device 110, maintaining slight pressure on the subject's fingers/thumb via cushion 114 by maintaining closing pressure on top section 112 and bottom section 111. Still maintaining closing pressure, the practitioner pulls applicator slide 118 to the outward position via knob 119, thereby moistening the subject's fingers/thumb, exposing the subject's fingers/thumb to image recorder 40, and pressing the subject's fingers/thumb onto image recorder 40. The practitioner then opens device 110 by relieving closing pressure, and removes the subject's fingers/thumb from device 110. With applicator slide 118 still in the outward position, the practitioner commences heating of image recorder 40 by activating timed actuation mechanism 70b.

Applicator slide 118 shown in FIG. 15 has wet pad 118d which is saturated with a liquid solvent-including substance by means of liquid solvent-including substance reservoir 118c. Wiper 118b is a non-porous blade which removes excess liquid solvent-including substance from the subject's fingers/thumb and returns liquid solvent-including substance to reservoir 118c. Dry pad 118a is a nearly moisture-free absorbent pad which, together with wiper 118b, provides the proper wetness level of the liquid solvent-including substance on the subject's fingers/thumb.

In practice of the present invention, the considerations for effectuating a quality print are analogous to those manifest in ink fingerprinting in that the practitioner seeks to exercise appropriate finesse with regard to both coating and imaging of the skin area to be printed; however, the preferred techniques for many embodiments of the present invention may not be identical to those frequently used for ink fingerprinting. "Tapping," "rubbing" and "dabbing-and-rubbing" are three coating techniques for the present invention, preference of which is dependent upon the particular embodiment and is easily ascertainable by the ordinarily skilled artisan.

Among tests of various basic organic solvents and of various products containing basic organic solvents, the two brands of fingertip moisteners tested, viz., TACKY FINGER and SORTKWIK, were found to be most amenable to and preferably performed via the "tapping" coating technique. When coating the skin area with an organic solvent from an image producer having a chemical matrix akin to that of these fingertip moisteners, it is believed that care should be taken by the practitioner of the present invention not to get the organic solvent-including substance in the skin grooves. It was additionally found for these two brands of fingertip moisteners that, before tapping fingers upon the surface of the image producer, it may be desirable to lightly rub with parallel motions the surface of the image producer so as to remove a thin dry film which may form thereon upon exposure to air.

The selection of the coating technique in accordance with this invention generally depends on the nature and character of the image producer, particularly in terms of viscosity and thixotropy. With regard to chemical matrix image producers, the particular thixotropic properties of certain chemical matrix image producers such as the fingertip moisteners tested provide a possible explanation for the apparent superiority of "tapping" coating technique for such chemical matrix image producers. It is believed that the wax-like viscosities of such chemical matrices may foster clogging of the skin grooves and consequent "printing in the grooves."

By contrast, testing of sponge-type, foam-type and rubber stamp fabric pad-type mechanical matrix image producers implementing propylene glycol as the liquid organic solvent demonstrated that, for these mechanical matrix image producers, no care need be exercised to avoid getting the liquid organic solvent in the subject's skin grooves, but care should be exercised to avoid coating the subject's skin area with excessive liquid organic solvent. However, even when excessive liquid organic solvent is applied, the excess can be wiped off, or rubbing pursuant to "dabbing-and-rubbing" technique can be performed, with excellent results.

Accordingly, for chemical matrix image producers such as the fingertip moisteners tested the matrix should just coat the skin ridges. For the present invention, this was found to be best accomplished by one or more light, quick taps upon the image producer, perpendicularly thereto, with the finger to be printed. In this manner, the skin area is approximately normal to the surface of the image producer and is not dragged along the surface of the image producer; the coating of the skin area is thereby optimally restricted to the top surfaces of the ridges. The appropriate number of taps for a given embodiment may be somewhat dependent upon the moistness of the chemical matrix, a dryer chemical matrix requiring a greater number of taps.

"Rolling" technique is akin to that technique often used for coating a skin area with ink for purposes of ink fingerprinting, wherein the skin area is made to contact an ink pad with a rolling motion. Tests on mechanical matrix image producers implementing propylene glycol as the liquid organic solvent (e.g., rubber stamp fabric pad containing propylene glycol) were inconclusive as to whether "rolling" coating technique would prove preferable for some embodiments of this invention, but "rolling" coating technique may at least be appropriate for some embodiments.

"Rubbing" entails one or more movements of the skin area along the surface of the image producer; when rubbing is performed then the preferred number and directions of such movements depend on the embodiment. "Rubbing" coating technique was found in tests to be preferable for sponge-type, foam-type and stamp pad-type mechanical matrix image producers.

When the skin area is then impressed onto the image recorder in practicing the present invention, it should be performed with single perpendicular pressing motion or with a rolling motion, the motion depending particularly upon the image recorder aspect of the practiced embodiment, performed with appropriate pressure and for an appropriate duration so as to maximize contrast and minimize smearing and obscuring, thereby optimizing the fingerprint. Ink fingerprinting impressing technique, in general, similarly requires perpendicularity of pressing motion along with appropriately applied pressure, but may require somewhat greater or lesser pressure applied to the surface and/or for somewhat longer or shorter duration than would be preferable for a given embodiment of the present invention.

Furthermore, the skin area should be timely impressed onto the image recorder within a few seconds after coating the skin area with either the pure organic solvent or the organic solvent plus chemical matrix. The solubilizingly active agent or agents in the organic solvent which has just been deposited upon the skin area may eventually evaporate and/or be absorbed.

Either or both the coating step and the impressing step in accordance with the present invention may be advantageously performed by a device or a combination of devices such as disclosed herein. These devices have compactness and serve to facilitate the proper execution of the coating and impressing steps. Fingerprinting devices 20 and 20' feature a tri-sectional pivotable configuration. Fingerprinting device 20 offers portability and one-hand practitioner operation. Based on the testing which was performed, it is believed that image producer 38 for the fingerprinting device 20 embodiment or the fingerprinting device 20' embodiment is preferably of an effective chemical matrix type or of the propylene glycol-containing mechanical matrix type.

For some embodiments either or both the coating and impressing steps according to this invention may be practiced in a manner similar to that generally used for conventional pigment-type ink fingerprinting, wherein the practitioner first manually guides the subject's distal phalanx skin areas directly onto an inkpad for the coating step and then manually guides the coated skin areas directly onto a paper material for the impressing step. In practicing the present invention, however, the customary "rolling" motion on the ink pad should be replaced by a "rubbing" motion on the solvent pad. Hence, the present invention may similarly be effectively practiced by means of direct manual guidance by the practitioner of the subject's distal phalanx skin areas upon either, or both, the image producer and the image recorder. Fingerprinting device 110 and applicator bottle 81 are intended for use with a solvent-including substance which is an appropriately flowable liquid, such as propylene glycol, and recording devices 90 and 90a are intended for use with any proper solvent-including substance.

For purposes of practicing embodiments involving such direct manual guidance onto both the image producer and the image recorder, it may provide no real advantage for the image producer and image recorder to be integrated into a single unit, especially for practice in stationary settings; the image producer and the image recorder may be housed in separate, independent units, e.g., image producing device 81 and image recording devices 90 and 90a). For practice in portable settings it may nevertheless be advantageous to include the image producer and the image recorder in a single unit which includes a compartment housing the image producer and a compartment housing the image recorder. For some such embodiments the single unit movably couples the compartment housing the image producer with the compartment housing the image recorder. This movable coupling may be accomplished, for example, pivotably ( e.g., as accomplished by tri-sectional pivotable configurational fingerprinting devices 20 and 20' disclosed herein), swivelingly or slidingly. Additionally, variations of single-compartment, dual-function units (e.g., image-producing, image-recording device 110) may be realized in accordance with this invention. The ordinarily skilled artisan is well acquainted with various configurations for a unit, either portable or stationary, which would appropriately serve to permit accessibility to an image producer and an image recorder, separately compartmentalized, or in a single compartment, in accordance with the present invention.

Several chemical compositions and commercial products were tested by the U.S. Navy for the present invention. Three thermal paper products were used for these tests: (1) Universal Office Products Premium Thermal Facsimile Paper, Product No. 35756, manufactured by United Stationers Supply Company, Des Plains, Il. 60016-1267; (2) HP (Hewlett Packard) Thermal Paper, product No. 92160 A; (3) Staples Thermal Fax Paper, SKU #236190.

For those organic solvents or organic solvent-containing products which were tested on all three thermal paper products, the results were comparable for all three thermal paper products. The only remarkable difference among the three thermal paper products was the bluish color produced by imprinting upon the HP thermal paper, presumably the designed image coloration of the HP product when used in fax machines, as distinguished from the grayish color produced by imprinting upon the Universal thermal paper and the Staples thermal paper. Although quality prints were obtained with all three thermal papers, the Staples thermal paper in some tests seems to exhibit less sensitivity than the other two brands tested, a characteristic which may be desirable for some embodiments. Many tests were performed on only the Staples thermal paper.

The color-producing mechanism is believed to be identical or analogous for commercially available thermal papers in general. Based on this understanding and the testing which was conducted it is believed that, regardless of chemical compositional differences that may exist among the many brands of thermal paper on the market, most if not virtually all of these brands may be appropriate as the image recorder, or as included in the image recorder, in accordance with the present invention.

There is a plethora of organic solvents in our known universe; their respective properties and degrees of solubilizing activity with respect to various substances are known, easily ascertainable or easily modifiable by the ordinarily skilled artisan. The testing which was conducted supported the reasonable theoretical conviction that numerous organic solvents may be used to darken thermal paper in accordance with the present invention. It is well within the purview of skill in the art to select organic solvents and commercially available thermal papers which are appropriately co-reactive in accordance with the present invention. It is also well within the purview of skill in the art to arrive at appropriate technique for optimizing fingerprint effectuation, using selected organic solvents and thermal papers, in accordance with the present invention.

Tests were conducted of the color-producing ("darkening") reaction of each of several organic solvents with respect to thermal paper. In these tests the organic solvent was either (i) finger-imprinted upon the thermal paper, or (ii) applied with cotton (e.g., via "q-tip") or in drops, in pure or diluted form, directly upon the thermal paper.

In one series of tests all three thermal papers were tested for reactivity to acetone, 1-propanol, 2-propanol and dehydrated analyzed reagent alcohol. All three thermal papers responded to all four chemicals. In another series of tests performed only on the Staples thermal paper, acetone, tetrahydrofuran, and N-methylpyrrolidinone were tested. All three non-alcohoholic solvents proved to be extremely active toward darkening the Staples thermal paper. The tetrahydrofuran not only darkened the thermal paper, but also appeared to leach out the color-producing compositions from the center of the application area, leaving a very dark perimeter ring.

This observed leaching phenomenon was also observed in other tests and points up the importance of avoiding "oversolubilizing" the thermal paper binder to the point that the color-producing compositions are also being solubilized, as demonstrated by migration of the color-producing compositions on the thermal paper. In other words, in practicing the present invention the organic solvent should not be overactive by virtue of excessive strength or concentration; the organic solvent should be of such strength and concentration as to solubilize the thermal paper binder only, and appreciably so, in accordance with this invention.

Several alcohols were also tested in this series of tests. In one set of trials, methanol, ethanol, isopropanol, ethylene glycol and glycerene were each first applied directly to Staples thermal paper to check for positive darkening response. Then the alcohols were finger-imprinted upon the thermal paper, the experimenters primarily seeking to determine the extent of darkening which occurred while fashioning "crude" fingerprints, but not seeking to improve or "fine tune" technique so as to render optimum fingerprints. Each alcohol was applied to a finger and allowed to dry somewhat before a fingerprint was attempted.

Methanol reacted weakly to the Staples thermal paper, but sufficient darkening was obtainable so as to produce a light fingerprint. Ethanol and isopropanol were both quite active, and somewhat respectable prints were obtained for each, though isopropanol may have proven slightly superior overall; they behaved similarly in that dark impressions were obtained immediately upon contact with the thermal paper. In those fingerprint trials wherein the skin area was excessively wet with ethanol or isopropanol, the resultant print was too dark and some print detail was obliterated.

Ethylene glycol left an immediate faint impression upon contact with the Staples thermal paper, but over time the image faded and came to be much less distinct. Glycerine similarly left an immediate faint impression, but the ensuing residual image was even less pronounced and barely discernible. For each of these liquids, the initial faint impression appears to have been due to a preferential "wetting" of the thermal paper due to the impressing thereon of the finger skin area; once the liquid was allowed to disperse evenly over the thermal paper, however, very little permanent darkening of the thermal paper actually occurred.

Isopropanol proved to be a highly active organic solvent vis-a-vis'the thermal paper binder material, perhaps too active in pure form for practicing most embodiments of the present invention. A one percent solution of isopropanol in glycerine was prepared in order to dilute the solubilizing activity of the isopropanol. A finger skin area was wetted with this mixture, host of the excess was blotted off, and the finger skin area was impressed upon the thermal paper; a respectable print was obtained.

Propylene glycol is an alcohol which proved to be an outstanding solubilizingly active chemical agent with respect to thermal paper binder material. Propylene glycol is a colorless, odorless, hygroscopic, viscous liquid of low toxicity which is prevalent in cosmetic and pharmaceutical products. Because of the superior results in terms of chemical activity which were obtained therewith in experiments, its low volatility, its viscosity, its various and widespread commercial availability and its virtually non-toxic quality, propylene glycol may be recommended for use as the solvent-including substance, or as the organic solvent included in the solvent-including substance, or as a solubilizingly active chemical agent included in the organic solvent included in the solvent-including substance, for practicing most embodiments of the present invention. It is reemphasized, however, that there is an abundance of known fundamental organic solvents in the world which may be appropriate for practicing the present invention in its multifarious embodiments.

In tests using various mechanical matrix image producers, pure propylene glycol served as the organic solvent which was contained by the mechanical matrix. It was shown that sponges, foam pads, rubber stamp fabric pads and paper towels, when appropriately moistened with propylene glycol, would all be effective mechanical matrices in practicing the present invention. Propylene glycol proved to be a highly effective solubilizingly active chemical agent with respect to the binder material of all three thermal paper image recorders tested.

Propylene glycol is a constituent of many cosmetic and pharmaceutical products on the market. So commonplace is its inclusion in some types of commercial products, e.g., in "solid stick" deodorants and/or antiperspirants, that propylene glycol is sometimes abbreviated "PG" in the list of ingredients on the product label.

Although it is reasonably speculated that propylene glycol may have played a role in the solubilization for many of the successful tests on commercial products, it has not been conclusively determined for these tests that propylene glycol is in fact the solubilizingly active chemical agent or among the solubilizingly active chemical agents; nor are the identities of any of the solubilizingly active chemical agents contained by the successful products conclusively determined.

The ease of applicability of the solvent-including substance to the skin area was an important factor in assessing the desirability of various vehicles tested for releasing the organic solvent. Three highly effective image producers, based on superior applicability, proved in tests to be commercially available products having a "beeswax" consistency and a moist, applicable surface.

Two such products which were successfully tested as pertains to the present invention were fingertip moisteners, one having the trade name "TACKY FINGER"(manufactured by Evans International Co., Inc., formerly known as Evans Specialty Co., Inc., 14 E. 15th Street, Richmond, Va. 23224-0189) and the other having the trade name "SORTKWIK"(manufactured by Lee Products Co., Inc., 800 East 80th Street, Minneapolis, Minn. 55420). Both fingertip moistener products were represented as containing propylene glycol. TACKY FINGER was represented by the manufacturer as containing glycerine USP, propylene glycol, isopropanol, sodium stearate, bicarbonate of soda, and water. SORTKWIK was represented by the manufacturer as containing glycerine, propylene glycol and stearic acid.

The third product successfully tested was Right Guard Sport deodorant stick, which the manufacturer (The Gillette Company, Per. Car Div., Boston, Mass. 02199) lists as containing propylene glycol, water, sodium stearate, fragrance, triclosan and FD & C blue no. 1.

The identity of the organic solvent in each successful solvent-including substance has not been established. It is not determined as to the organic solvent whether in fact propylene glycol is the only solubilizingly active chemical agent or is one of a plurality of solubilizingly active chemical agents; nor are known the relative degrees of activity, if there is a plurality of solubilizingly active chemical agents. In any case, the TACKY FINGER and SORTKWIK fingertip moisteners and the Right Guard Sport deodorant appear to have beneficial attributes with respect no the thermal paper, not only in terms of chemical activity but also in terms of viscosity and "wettability."

Original Tussy Cream Deodorant did not list propylene glycol on its label but nevertheless proved to be an effective image producer, the impression developing upon the Universal and Staples thermal papers with a greenish color instead of the more usual grayish color. The print on the HP thermal paper was the accustomed blue color for that thermal paper. The label for Original Tussy Cream Deodorant listed the following ingredients: water, glyceryl stearate, cetyl esters, aluminum sulfate, glycerin, sodium sulfate, aluminum hydroxide, sodium lauryl sulfate, cetyl alcohol, carrageenan, fragrance, titanium dioxide, lanolin, mineral oil, petrolatum iron oxides, talc.

In an attempt to simulate the TACKY FINGER or SORTKWIK material, isopropanol, ethylene glycol, and glycerine were obtained from the laboratory into a fairly hard wax. Unfortunately, there was poor miscibility of these materials; the wax remained quite hard and did not achieve the desired soft consistency. Nevertheless, it was still possible to rub some of the material onto a finger and to render a reasonable print on the Staples thermal paper. It is well within the capability of the ordinarily skilled artisan, in practicing the present invention, not only to produce a formulation similar to that of these fingertip moisteners or of the Right Guard Sport deodorant, but also to adjust the organic solvent content of the formulation in accordance with desired solubilizing activity levels.

In general, in the testing of commercially available cosmetic and office products which was performed, only some of the products proved to be successful chemical matrix image producers. In fact, not all of the products which representationally contained propylene glycol proved to contain one or more solubilizingly active chemical agents with respect to the thermal paper binder material.

The group of tests for the following products did not produce promising results. However, it is emphasized that these tests were performed in cursory fashion; these tests should be viewed as preliminary in nature and not as supporting meaningful conclusions as to the appropriateness, or lack thereof, of a given commercial product or any of its ingredients for practicing the present invention or any of the multifarious embodiments thereof. The products as follows did not list propylene glycol on the label as an ingredient: Right Guard Sport Anti-Perspirant & Deodorant stick; and, Degree Anti-Perspirant & Deodorant stick. The products as follows listed propylene glycol on the label as an ingredient: Wet Ones Moist Towelettes with Aloe manufactured by L & F Products; CVS Baby Wipes; and, jelly bean-flavored and strawberry-flavored Lip Smacker Fun Flavored Lip Gloss, manufactured by Bonnie Bell. In some cases there was no discernible impression, or an initial faint impression soon virtually disappeared. It is speculated that each of the products which advertised propylene glycol as an ingredient may have contained an insufficient amount of propylene glycol to be effective.

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. Method for generating a print of human skin, comprising:

coating an area of said skin with a substance which includes an organic solvent;

impressing said area onto an image recorder; and withdrawing said area from said image recorder;

said image recorder including a substrate, an electron-donating chromogenic composition and an electron-accepting developer composition which are dispersed on said substrate, and a binder material which is substantially soluble to said organic solvent and which generally maintains separation of said electron-donating chromogenic composition and said electron-accepting developer composition until said impressing, whereupon some said binder material is solubilized by at least some said organic solvent.

2. Method for generating a print as in claim 1, wherein said organic solvent is contained by a mechanical matrix.

3. Method for generating a print as in claim 1, wherein said organic solvent is contained by a chemical matrix whereby the combination of said chemical matrix and said organic solvent is macroscopically homogeneous.

4. Method for generating a print as in claim 1, wherein said organic solvent includes at least one alcohol.

5. Method for generating a print as in claim 1, wherein said organic solvent includes propylene glycol.

6. Method for generating a print as in claim 1, further comprising applying heat to said image recorder.

7. Method for generating a print as in claim 6, wherein said applying heat renders the temperature of said image recorder approximately 100 degrees Fahrenheit.

8. Method for generating a print as in claim 6, wherein said applying heat includes using a device selected from the group consisting of a heat lamp, an incandescent lamp, a hair dryer, a heat gun and a hot plate.

9. Method for generating a print of human skin, comprising:
 coating an area of said skin with a substance which includes an organic solvent;
 impressing said area onto thermal paper material which includes a chromogenic composition, a developer composition and a binder ingredient, said binder ingredient being substantially soluble to said organic solvent; and
 withdrawing said area from said thermal paper material;
 whereby, as a result of said solubilizing of some said binder ingredient by at least some said organic solvent, some said chromogenic composition and some said developer composition interact, a visible impression is formed on said thermal paper, and said visible impression develops into said print.

10. Method for generating a print as in claim 9, wherein said organic solvent is contained by a mechanical matrix.

11. Method for generating a print as in claim 9, wherein said organic solvent is contained by a chemical matrix whereby the combination of said chemical matrix and said organic solvent is macroscopically homogeneous.

12. Method for generating a print as in claim 9, wherein said organic solvent includes at least one alcohol.

13. Method for generating a print as in claim 9, wherein said organic solvent includes propylene glycol.

14. Method for generating a print as in claim 9, further comprising applying heat to said image recorder.

15. Method for generating a print as in claim 14, wherein said applying heat renders the temperature of said image recorder approximately 100 degrees Fahrenheit.

16. Method for generating a print as in claim 14, wherein said applying heat includes using a device selected from the group consisting of a heat lamp, an incandescent lamp, a hair dryer, a heat gun and a hot plate.

17. Apparatus for generating a print of human skin, comprising:
 an image producer, said image producer including a matrix and an organic solvent which is contained by said matrix whereby, when an area of said skin contacts said image producer, said image producer delivers onto said skin area a quantity of substance, thereby coating said skin area with said substance quantity, said substance quantity including a portion of said organic solvent; and
 an image recorder for being impressed upon and withdrawn from by said coated skin area, said image recorder including a substrate, an electron-donating chromogenic composition and an electron-accepting developer composition which are dispersed on said substrate, and a binder material which is substantially soluble to said organic solvent;
 wherein said binder material generally maintains separation of said electron-donating chromogenic composition and said electron-accepting developer composition until said being impressed upon, whereupon some said binder material is solubilized by at least some said organic solvent portion which is included in said substance quantity with which said skin area has been coated.

18. Apparatus for generating a print as in claim 17, wherein said matrix is selected from the group consisting of mechanical matrix and chemical matrix, said chemical matrix containing said organic solvent whereby the combination of said chemical matrix and said organic solvent is macroscopically homogeneous.

19. Apparatus for generating a print as in claim 17, wherein said organic solvent includes at least one alcohol.

20. Apparatus for generating a print as in claim 17, wherein said organic solvent includes propylene glycol.

21. Apparatus for generating a print as in claim 17, further comprising means for applying heat to said image recorder.

22. Apparatus for generating a print as in claim 21, wherein said applying heat renders the temperature of said image recorder approximately 100 degrees Fahrenheit.

23. Apparatus for generating a print as in claim 21, wherein said means for applying heat includes a device and means for activating said device, said device selected from the group consisting of a heat lamp, an incandescent lamp, a hair dryer, a heat gun and a hot plate.

24. Apparatus for generating a print as in claim 21, further comprising means for actuating and deactuating said means for applying heat.

25. Apparatus for generating a print as in claim 17, further comprising a first compartment for housing said image producer and a second compartment for housing said image recorder.

26. Apparatus for generating a print as in claim 25, further comprising means for movably coupling said first compartment and said second compartment.

27. Apparatus for generating a print as in claim 17, wherein said image producer and said image recorder are each included in a separate unit.

28. Method for generating a print as in claim 1, wherein:
 said coating includes causing said area to contact an image producer which includes a matrix and said organic solvent which is contained by said matrix, whereby said image producer delivers onto said area a quantity of said substance, thereby coating said area with said quantity, said quantity including a portion of said organic solvent; and
 upon said impressing, some said binder material is solubilized by at least some said portion which is included in said quantity with which said area has been coated.

29. Method for generating a print as in claim 9, wherein said coating includes causing said area to contact an image producer which includes a matrix and said organic solvent which is contained by said matrix, whereby said image producer delivers onto said area a quantity of said substance, thereby coating said area with said quantity, said quantity including a portion of said organic solvent.

* * * * *